(12) United States Patent  (10) Patent No.: US 8,135,457 B2
Kodama  (45) Date of Patent: Mar. 13, 2012

(54) APPARATUS FOR MEASUREMENT OF LIVING BODY

(75) Inventor: Miyuki Kodama, Tokyo (JP)

(73) Assignee: Tanita Corporation, Tokyo (JP)

( * ) Notice: Subject to any disclaimer, the term of this patent is extended or adjusted under 35 U.S.C. 154(b) by 1705 days.

(21) Appl. No.: 11/300,499

(22) Filed: Dec. 15, 2005

(65) Prior Publication Data

US 2006/0094977 A1   May 4, 2006

Related U.S. Application Data

(62) Division of application No. 10/196,944, filed on Jul. 18, 2002, now Pat. No. 7,147,603.

(30) Foreign Application Priority Data

Jul. 19, 2001   (JP) ................. 2001-219735

(51) Int. Cl.
   *A61B 5/05*   (2006.01)
(52) U.S. Cl. ........................................ 600/547
(58) Field of Classification Search .......... 600/547, 600/300, 531, 301, 500, 503, 587; 702/131
   See application file for complete search history.

(56) References Cited

U.S. PATENT DOCUMENTS

| | | | | | |
|---|---|---|---|---|---|
| 2,933,082 | A | * | 4/1960 | Billin | 600/531 |
| 6,030,342 | A | * | 2/2000 | Amano et al. | 600/301 |
| 6,487,445 | B1 | | 11/2002 | Serita et al. | |
| 6,643,542 | B1 | * | 11/2003 | Kawanishi | 600/547 |
| 2002/0052697 | A1 | | 5/2002 | Serita | |

FOREIGN PATENT DOCUMENTS

| | | |
|---|---|---|
| BE | 894 439 A | 1/1983 |
| EP | 1 183 994 A1 | 3/2002 |
| EP | 1 219 238 A1 | 7/2002 |
| JP | 5-49050 | 7/1993 |
| JP | 11216121 | 8/1999 |
| JP | 2001-061806 | 3/2001 |
| WO | WO 01/15600 | 3/2001 |
| WO | WO 01/28495 | 4/2001 |

OTHER PUBLICATIONS

European Search Report, issued in corresponding European Patent Application No. 07015971.0-1526, dated Oct. 4, 2007.
R. Tverskaya et al., "Comparison of Several Equations and Derivation of a New Equation for Calculating Basal Metabolic Rate in Obese Children", Journal of the American College of Nutrition, Wilmington, NC, US, vol. 17, No. 4, Aug. 1998, pp. 333-336, XP001034857, ISSN: 0731-5724.
T. N. Sathyaprabha "Basal Metabolic Rate and Body Composition in Elderly Indian Males", XP008002992 P.D. Sep. 2000, pp. 179-184 Indian J Physiol Pharmacol 2000; 44 (2).
United States Office Action issued in U.S. Appl. No. 11/300,500 dated Jun. 4, 2010.
United States Office Action issued in U.S. Appl. No. 11/300,500, mailed Jan. 11, 2011.

* cited by examiner

*Primary Examiner* — Brian Szmal
(74) *Attorney, Agent, or Firm* — McDermott Will & Emery LLP

(57) ABSTRACT

Disclosed is an apparatus for measurement of a living body, comprising: a personal data input unit; a basal metabolism input unit; a standard value storage unit; a comparison unit; and a display unit. According to the invention the personal data input unit enters at least an age of a person to be measured, the basal metabolism input unit enters a basal metabolism of the person to be measured, and the standard value storage unit stores standard values of basal metabolism according to the ages. Furthermore, the comparison unit compares the basal metabolism entered by the input unit with the standard values of basal metabolism according to the ages stored in said storage unit, and calculates a basal metabolic age indicating what age the basal metabolism of the person to be measured corresponds to. Then, the display unit displays the information about the calculated basal metabolic age.

3 Claims, 25 Drawing Sheets

FIG.10

Standard of Basal Metabolism for Different Ages
(Basal Metabolism per Body Weight: kcal / kg)
by Ministry of Health and Welfare

| Age | Male | Female |
|---|---|---|
| 1~2 | 61.0 | 59.7 |
| 3~5 | 54.8 | 52.2 |
| 6~8 | 44.3 | 41.9 |
| 9~11 | 37.4 | 34.8 |
| 12~14 | 31.0 | 29.6 |
| 15~17 | 27.0 | 25.3 |
| 18~29 | 24.0 | 23.6 |
| 30~49 | 22.3 | 21.7 |
| 50~59 | 21.5 | 20.7 |
| 60~69 | 21.5 | 20.7 |
| 70~ | 21.5 | 20.7 |

FIG.16

| Sex | Proper Range | | Corpulent |
|---|---|---|---|
| | Less than 30 years old | Not less than 30 years old | |
| Male | 14~20% | 17~23% | Over 25% |
| Female | 17~24% | 20~27% | Over 30% |

FIG.17

| Visceral Fat Area | Visceral Fat Level | Result |
|---|---|---|
| Less than 100cm² | Less than 10 | OK |
| 100≦X<150cm² | 10≦X<15 | Need slight care (Somewhat dangerous) |
| Over 150cm² | Over 15 | Need essential care (Highly dangerous) |

FIG.18

List for evaluating metabolic age based on basal metabolism per body weight(kcal / kg)
(Prepared with reference to "Standard of Basal Metabolism for Different Ages" by Ministry of Health and Welfare)

| Male(kcal / kg) | Female(kcal / kg) | Metabolic Age |
|---|---|---|
| $37.4 \leq X$ | $34.8 \leq X$ | Less than 10 |
| $37.4 > X \geq 27$ | $34.8 > X \geq 25.3$ | First half of tens |
| $27 > X \geq 24$ | $25.3 > X \geq 23.6$ | Latter half of tens |
| $24 > X \geq 22.3$ | $23.6 > X \geq 21.7$ | Twenties |
| $22.3 > X \geq 21.5$ | $21.7 > X \geq 20.7$ | Thirties to fifties |
| $21.5 > X$ | $20.7 > X$ | Over fifties |

FIG.19

| Basal Metabolism \ Visceral Fat | <Higher> | | |
|---|---|---|---|
| | Youthful and healthy-looking, sport-man type, lower dangerous level of visceral fat, and higher level of metabolism. Keep current body shape! Exercise program recommended:①-C | Sport-man type, higher level of metabolism, but slightly higher dangerous level of visceral fat. Burn visceral fat by utilizing higher level of metabolism! Exercise program recommended:②-C | Sport-man type, higher level of metabolism, but higher dangerous level of visceral fat. Pay attention to living habit and burn visceral fat by utilizing higher level of metabolism! Exercise program recommended:③-C |
| <Standard> | Lower dangerous level of visceral fat, and standard level of metabolism. No specific problem present. Keep current body shape! Exercise program recommended:①-B | Slightly higher dangerous level of visceral fat, and standard level of metabolism. Increase metabolism to burn visceral fat with aerobics exercise! Exercise program recommended:②-B | Higher dangerous level of visceral fat. Pay attention to living habit and increase metabolism to burn visceral fat with aerobics exercise! Exercise program recommended:③-B |
| <Lower> | Dangerous level of visceral fat is currently lower, but because of lower level of metabolism it may be possible to accumulate visceral fat with age. Exercise program recommended:①-A | Slightly higher dangerous level of visceral fat, and lack of exercise with lower level of metabolism. Do exercise to increase metabolism and to burn visceral fat! Exercise program recommended:②-A | Higher dangerous level of visceral fat, and lack of exercise with lower level of metabolism. Pay attention to living habit! Do exercise to increase metabolism and to burn visceral fat! Exercise program recommended:③-A |
| | <Less than 100cm²> <Less than level 10> | <100 to 150cm²> <Level 10 to 15> | <Over 150cm²> <Over level 15> |

FIG.20

| | ①-C | ②-C | ③-C |
|---|---|---|---|
| | <Before going to bed> Stretch exercise for relaxing and muscle training (mainly for abdominal muscle) for keeping body shape for period of 5 min. | <Day Time> Fast walking for period of 30 min. <Before going to bed> Stretch exercise for relaxing and muscle training (mainly for abdominal muscle) for keeping body shape for period of 5 min. | <Day Time> Fast walking for period of 1 hour or riding a bicycle for period of 30 min. <Before going to bed> Stretch exercise for relaxing and muscle training (mainly for abdominal muscle) for keeping body shape for period of 5 min. |
| | ①-B | ②-B | ③-B |
| | <Before going to bed> Muscle training (for a whole body) for increasing metabolism and tightening the body for period of 10 min. | <Day Time> Fast walking for period of 30 min. <Before going to bed> Muscle training (for a whole body) for increasing metabolism and tightening the body for period of 10 min. | <Day Time> Fast walking for period of 1 hour or riding a bicycle for period of 30 min. <Before going to bed> Muscle training (for a whole body) for increasing metabolism and tightening the body for period of 10 min. |
| | ①-A | ②-A | ③-A |
| | <Before going to bed> Slightly hard, muscle training (for a whole body) for increasing metabolism for period of 15 min. | <Day Time> Fast walking for period of 30 min. <Before going to bed> Slightly hard, muscle training (for a whole body) for increasing metabolism for period of 15 min. | <Day Time> Fast walking for period of 1 hour or riding a bicycle for period of 30 min. <Before going to bed> Slightly hard, muscle training (for a whole body) for increasing metabolism for period of 15 min. |

FIG.21

| Basal Metabolism \ BMI | <Less than 18.5> | <18.5 to 25> | <Over 25> |
|---|---|---|---|
| <Higher> | Athlete type having a tightened slim body and difficult to be fat. Refer to exercise program ①-C in order to maintain muscle. | Healthy-looking, athlete type difficult to be fat because of a lot of muscle and higher level of metabolism. Refer to exercise program ②-C in order to maintain muscle. | Solid build, athlete type having a lot of muscle and higher level of metabolism. Refer to exercise program ③-C "an aerobics exercise for reduction of fat" in order not to increase fat. |
| <Standard> | Healthy-looking, smart type, rather slim, but having standard level of metabolism and muscle. Refer to exercise program ①-B in order to maintain muscle. | Standard level of metabolism and muscle. Refer to exercise program ②-B "an aerobics exercise and an exercise for maintaining muscle" in order to maintain the body shape without any strain. | Because of standard level of metabolism do exercise little more to additionally burn fat for healthy body. Refer to exercise program ③-B. |
| <Lower> | Rather slim, lower level of metabolism. Because of lack of exercise and higher possibility of fat, refer to exercise program ①-A "an exercise for increasing muscle and metabolism". | Because of poor of muscle, metabolism is lower. Refer to exercise program ②-A for increasing muscle and metabolism. | A lot of fat present and lower level of metabolism. Refer to exercise program ③-A "an aerobics exercise for reduction of fat" in order to reduce fat. |

APPARATUS FOR MEASUREMENT OF LIVING BODY

RELATED APPLICATIONS

This application is a divisional of Application Ser. No. 10/196,944, filed Jul. 18, 2002 now U.S. Pat. No. 7,147,603, which claims priority of Japanese Application No. 2001-219735, filed Jul. 19, 2001, the contents of which are hereby incorporated by reference.

BACKGROUND OF THE INVENTION

1. Field of the Invention

The present invention relates to an apparatus for measurement of a living body, having capability of intelligibly and understandably displaying living body information such as basal metabolism, visceral fat area, etc. of a person to be measured.

2. Prior Art

In the past, in order to know accurate basal metabolism of a person to be measured, an expensive and extensive apparatus was necessary. Additionally, many loads and measuring conditions are required, and the person to be measured had to keep at rest for a longer period of time with wearing a face-mask and a mouthpiece.

In addition, only a specialist could handle the measurement apparatus and evaluate the measured results. As such the general public can hardly perform their own tests to obtain an accurate measure of their own basal metabolism.

For those reasons, a statistically standard basal metabolism value has been used in most cases to determine the basal metabolism. The statistically standard basal metabolism value is obtained, for example in Japan, by multiplying a standard value of basal metabolism on the basis of gender and age according to Health Service Bureau of Former Ministry of Health and Welfare by body weight. This standard value has been used despite the importance of a relationship between adiposis and basal metabolism.

Moreover, the living body information such as pulse rate, blood pressure, body fat rate, visceral fat area, basal metabolism, etc., have generally been displayed as the numerical values of measurement results.

The basal metabolism, however, is considered to be directly proportional to fat-free mass rather than to actual body weight. The basal metabolism determined using the above-mentioned method is only suitable for a human having a standard body build and a standard body composition, because body composition is a strong effective factor. However, a calculated value of basal metabolism tends to be higher than an observed value of basal metabolism in a pycnic type (i.e., a human with a high fat rate) who has a heavy body weight and a large amount of fat. On the other hand, a calculated value of basal metabolism tends to be lower than an observed value of basal metabolism in a slim and muscular man (i.e., a human with a low fat rate). Therefore, the above-mentioned method for calculating basal metabolism is not preferable from the viewpoint of guidance for adiposis.

Furthermore, as described earlier, the living body information such as pulse rate, blood pressure, body fat rate, visceral fat area, basal metabolism, etc., have frequently been displayed as the numerical values, but those numerical values are difficult for the person to be measured to understand the measurement result.

In view of the above an object of the present invention is to provide an apparatus for measurement of a living body, having capability of calculating basal metabolism of a person to be measured according to various types of body build.

Another object of the present invention is to provide an apparatus for measurement of a living body, having capability of intelligibly and understandably displaying any change in living body information to a person to be measured.

SUMMARY OF THE INVENTION

According to one aspect of the present invention there is provided an apparatus for measurement of a living body, comprising: a personal data input unit; a basal metabolism input unit; a standard value storage unit; a comparison unit; and a display unit, wherein said personal data input unit enters at least an age of a person to be measured, said basal metabolism input unit enters a basal metabolism of the person to be measured, said standard value storage unit stores standard values of basal metabolism according to the ages, said comparison unit compares the basal metabolism entered by said input unit with the standard values of basal metabolism according to the ages stored in said storage unit, and calculates a basal metabolic age indicating what age the basal metabolism of the person to be measured corresponds to, and said display unit displays the information about the calculated basal metabolic age.

In one embodiment of the present invention the basal metabolism of the person to be measured entered by said basal metabolism input unit is calculated on the basis of fat-free mass of the person to be measured.

In another embodiment of the present invention said fat-free mass is calculated on the basis of bioelectrical impedance.

In further embodiment of the present invention said fat-free mass is calculated on the basis of the thickness of subcutaneous fat.

In yet further embodiment of the present invention said basal metabolism input unit calculates according to analysis of expiration.

According to another aspect of the present invention there is provided an apparatus for measurement of a living body, comprising: a personal data input unit; a basal metabolism input unit; a data storage unit; a comparison unit; and a display unit, wherein said personal data input unit enters at least an age of a person to be measured, said basal metabolism input unit enters a basal metabolism of the person to be measured, said data storage unit stores the basal metabolism entered by said input unit, said comparison unit compares the latest basal metabolism entered by said input unit with the already stored basal metabolism, and said display unit displays the result of comparison.

In one embodiment of the present invention the apparatus for measurement of a living body further comprises a standard value storage unit, and in which said standard value storage unit stores standard values of basal metabolism according to the ages, said comparison unit compares the basal metabolism entered by said input unit with the standard values of basal metabolism according to the ages stored in said storage unit, and calculates a basal metabolic age indicating what age the basal metabolism of the person to be measured corresponds to, and said display unit displays the information about the calculated basal metabolic age.

According to further aspect of the present invention there is provided an apparatus for measurement of a living body, comprising: a personal data input unit; a basal metabolism input unit; a standard value storage unit; an arithmetic unit; a comparison unit; and a display unit, wherein said personal data input unit enters at least an age of a person to be measured, said basal metabolism input unit enters a basal metabolism of the person to be measured, said standard value storage unit stores standard values of basal metabolism according to the ages, said arithmetic unit calculates "BMI" on the basis of the personal data, said comparison unit compares the basal metabolism entered by said input unit with the standard values of basal metabolism according to the ages stored in said storage unit, and said display unit displays the information about the relation between the result of comparison and said "BMI".

In one embodiment of the present invention the apparatus for measurement of a living body further comprises an advice information storage unit, and in which said advice information storage unit stores an advice information according to the relation between the basal metabolism and said "BMI", said comparison unit selects the advice information for the person to be measured based on the result of comparison and said "BMI", and said display unit displays the selected advice information.

In another embodiment of the present invention said advice information stored in said advice information storage unit includes at least one of the advice information for type of exercise, content of exercise and time interval of exercise suitable for the age of the person to be measured.

In further embodiment of the present invention said comparison unit compares the basal metabolism entered with the standard values of basal metabolism according to the ages, and calculates a basal metabolic age indicating what age the basal metabolism of the person to be measured corresponds to, and said display unit displays the information about the calculated basal metabolic age.

According to yet further aspect of the present invention there is provided an apparatus for measurement of a living body, comprising: a personal data input unit; a visceral fat area input unit; a standard value storage unit; a comparison unit; and a display unit, wherein said personal data input unit enters at least an age of a person to be measured, said visceral fat area input unit enters a visceral fat area of the person to be measured, said standard value storage unit stores standard values of visceral fat area according to the ages, said comparison unit compares the visceral fat area entered by said input unit with the standard values of visceral fat area according to the ages stored in said storage unit, and calculates a visceral fat age indicating what age the visceral fat area of the person to be measured corresponds to, and said display unit displays the information about the calculated visceral fat age.

In one embodiment of the present invention said visceral fat area of the person to be measured entered by said visceral fat area input unit is calculated on the basis of the girth of abdomen of the person to be measured.

In another embodiment of the present invention said visceral fat area of the person to be measured entered by said visceral fat area input unit is calculated on the basis of the bioelectric impedance of the person to be measured.

In further embodiment of the present invention said visceral fat area of the person to be measured entered by said visceral fat area input unit is calculated on the basis of the thickness of subcutaneous fat of the person to be measured.

According to yet further aspect of the present invention there is provided an apparatus for measurement of a living body, comprising: a personal data input unit; a visceral fat area input unit; a data storage unit; a comparison unit; and a display unit, wherein said personal data input unit enters at least an age of a person to be measured, said visceral fat area input unit enters a visceral fat area of the person to be measured, said data storage unit stores the visceral fat area entered by said input unit, said comparison unit compares the latest visceral fat area entered by said input unit with the visceral fat area already stored in said data storage unit, and said display unit displays the result of comparison.

In one embodiment of the present invention said comparison unit compares the visceral fat area entered with the standard values of visceral fat area according to the ages, and calculates a visceral fat age indicating what age the visceral fat area of the person to be measured corresponds to, and said display unit displays the information about the calculated visceral fat age.

According to yet further aspect of the present invention there is provided an apparatus for measurement of a living body, comprising: a personal data input unit; a visceral fat area input unit; an arithmetic unit;

a comparison unit; and a display unit, wherein said personal data input unit enters at least an age of a person to be measured, said visceral fat area input unit enters a visceral fat area of the person to be measured, said arithmetic unit calculates the basal metabolism of the person to be measured, said comparison unit compares the visceral fat area entered by said input unit with the basal metabolism calculated by said arithmetic unit, and said display unit displays the result of comparison.

In one embodiment of the present invention the apparatus for measurement of a living body further comprises an advice information storage unit, and in which said advice information storage unit stores an advice information according to the relation between the basal metabolism and the visceral fat, said comparison unit selects the advice information for the person to be measured based on the result of comparison, and said display unit displays the selected advice information.

In another embodiment of the present invention the apparatus for measurement of a living body further comprises a standard value storage unit, and in which said standard value storage unit stores standard values of basal metabolism according to the ages and standard values of visceral fat area according to the ages, said comparison unit compares the basal metabolism entered with the standard values of basal metabolism according to the ages and calculates a basal metabolic age indicating what age the basal metabolism of the person to be measured corresponds to, and further compares the visceral fat area entered with the standard values of visceral fat area according to the ages and calculates a visceral fat age indicating what age the visceral fat area of the person to be measured corresponds to, and said display unit displays the information about the calculated basal metabolic age and the calculated visceral fat age.

BRIEF DESCRIPTION OF THE DRAWINGS

The present invention will be described in more detail with reference to the accompanying drawings, in which:

FIG. 10 is a list of standard of basal metabolism according to age;

FIG. 16 is a list showing body fat rate for use in evaluation;

FIG. 17 is a list showing visceral fat area for use in evaluation;

FIG. 18 is a list showing basal metabolic age for use in evaluation;

FIG. 19 is a list showing basal metabolism and visceral fat mass for use in evaluation;

FIG. 20 is a list showing exercise programs to be conducted according to the result of evaluation;

FIG. 21 is a list showing basal metabolism and BMI for use in evaluation;

DESCRIPTION OF THE PREFERRED EMBODIMENT

Figure 1:
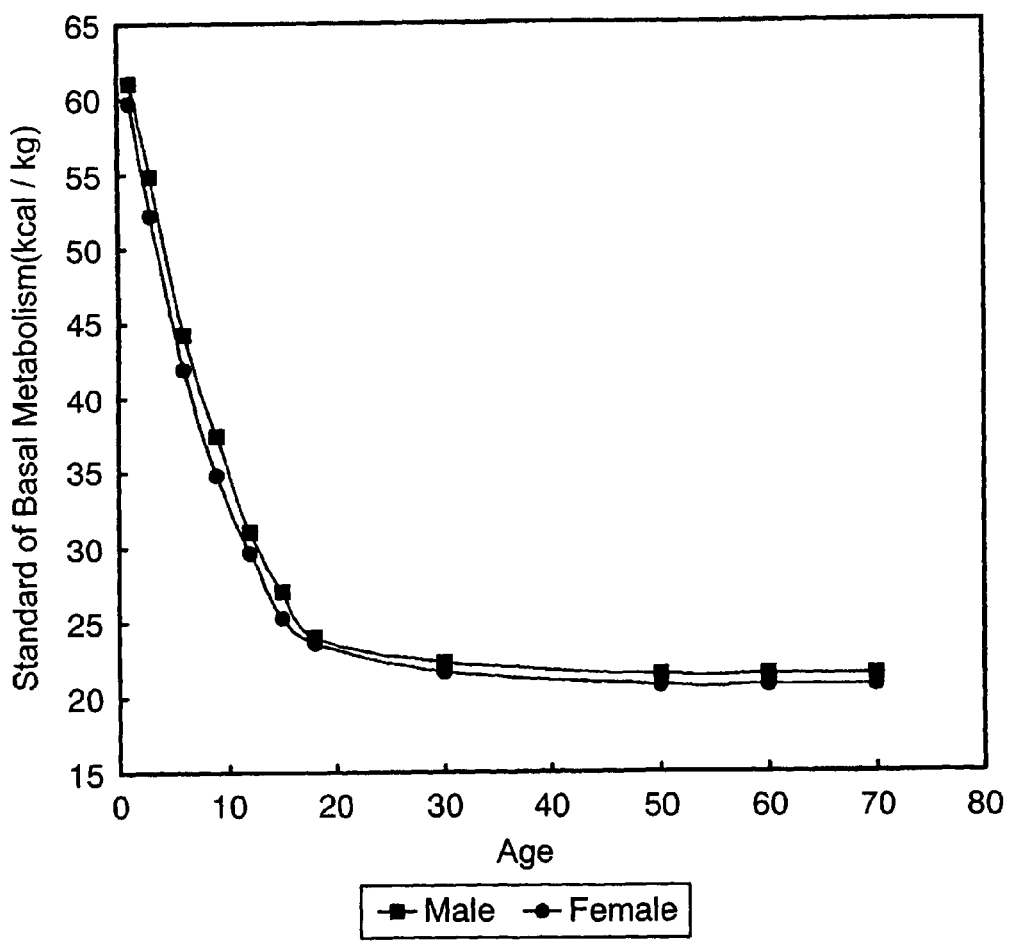
FIG. 1 is a graph illustrating a relationship between standard of basal metabolism and age.
Figure 2:
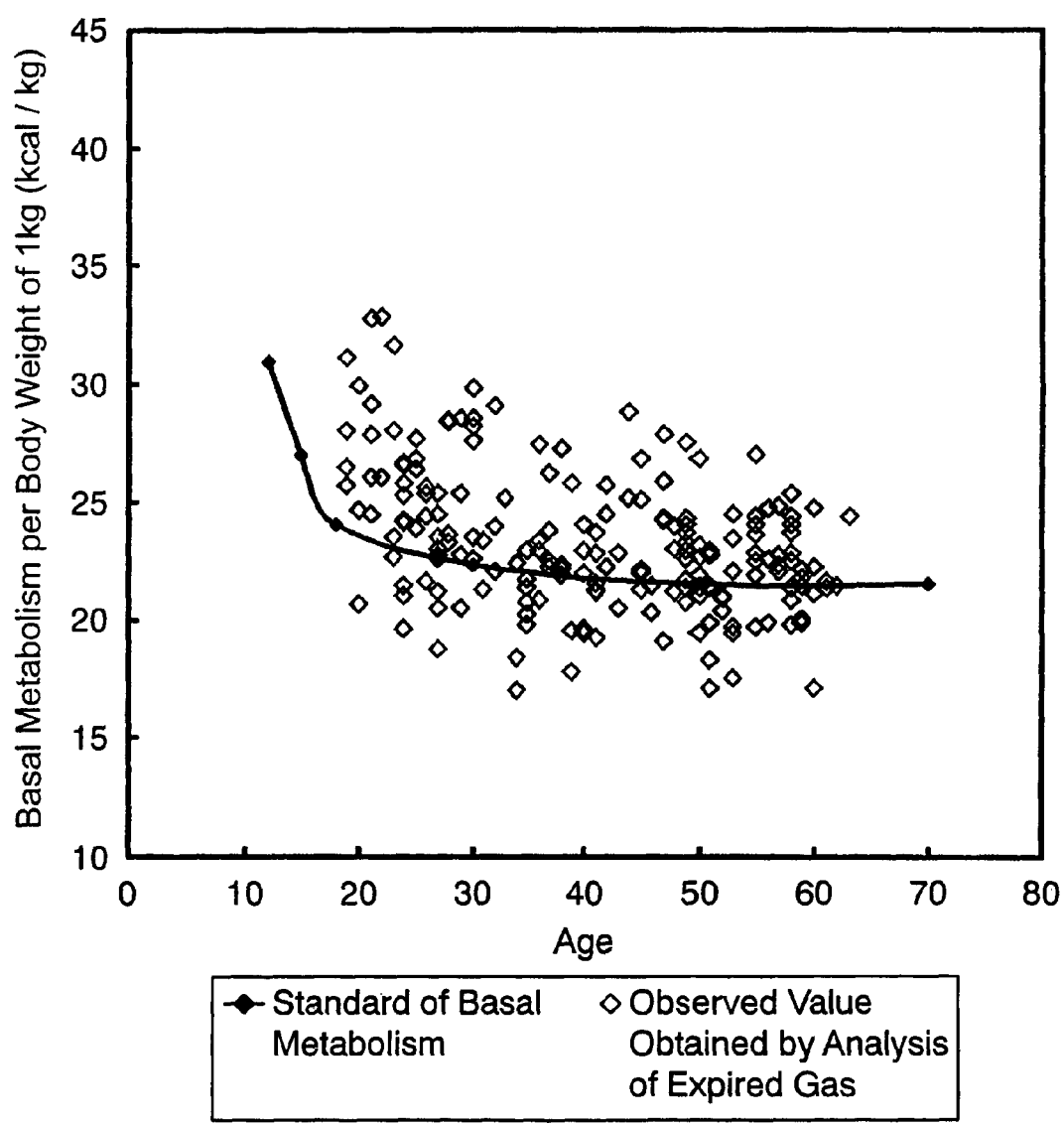
FIG. 2 is a graph illustrating a relationship between basal metabolism per body weight and age.

First of all, the measurement of basal metabolism will be described. As shown in FIG. 1, the inventors of the present invention have reviewed the standard values of basal metabolism provided by the Health Service Bureau of Former Ministry of Health and Welfare and have determined that those values are inversely proportional to an age of a person to be measured. In addition, as shown in FIG. 2, the inventors of the present invention have observed that the basal metabolism per body weight is also inversely proportional to an age.

Accordingly the inventors of the present invention have found that a reciprocal of an age in addition to fat-free mass is preferably utilized when calculating the basal metabolism. In particular, the basal metabolism can be calculated using the following formula:

$$BMR = A_1 \times FFM + B_1 \times (1/\text{age}) + C_1$$

Where BMR is basal metabolism (kcal/kg), FFM is fat-free mass (kg), and $A_1$, $B_1$ and $C_1$ are constants.

Figure 3:
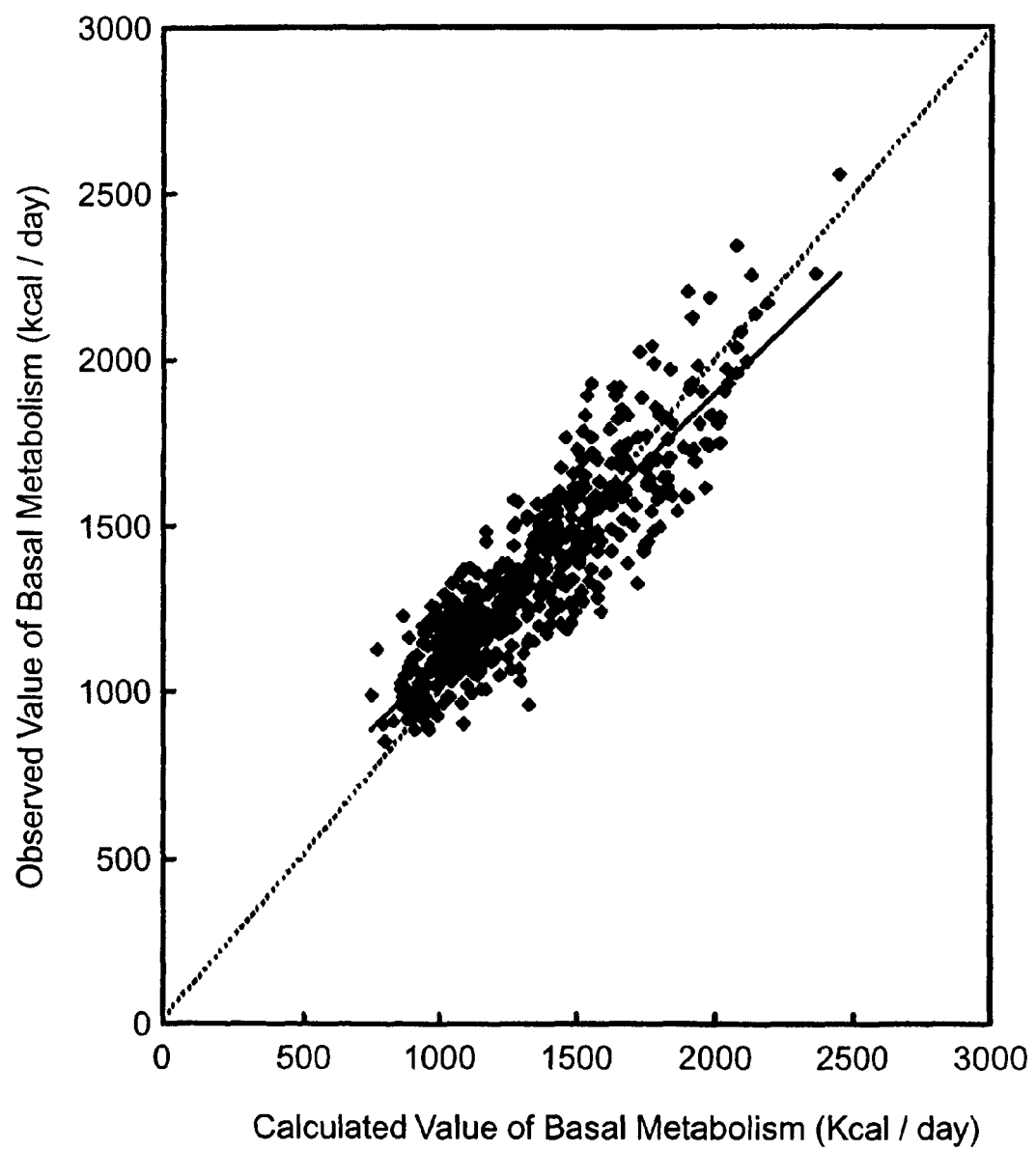
FIG. 3 is a graph illustrating a relationship between observed value of basal metabolism and calculated value of basal metabolism, taking into account of a reciprocal of an age.
Figure 4:
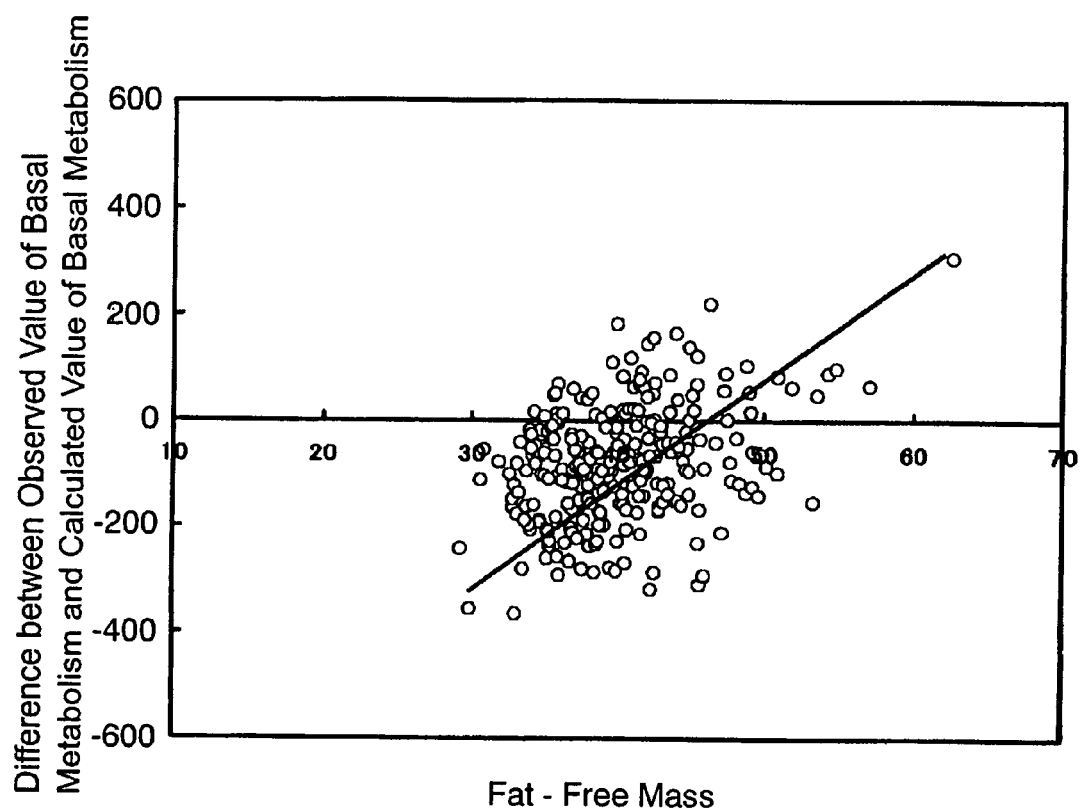
FIG. 4 is a graph illustrating a relationship between difference between observed value of basal metabolism and calculated value of basal metabolism and fat-free mass.

As shown in FIG. 3, a correlation coefficient between the basal metabolism obtained using the above-mentioned formula and the observed basal metabolism is 0.870. As shown in FIG. 4, the difference between an observed value and a calculated value against fat-free mass is half of the conventional data.

Figure 5:
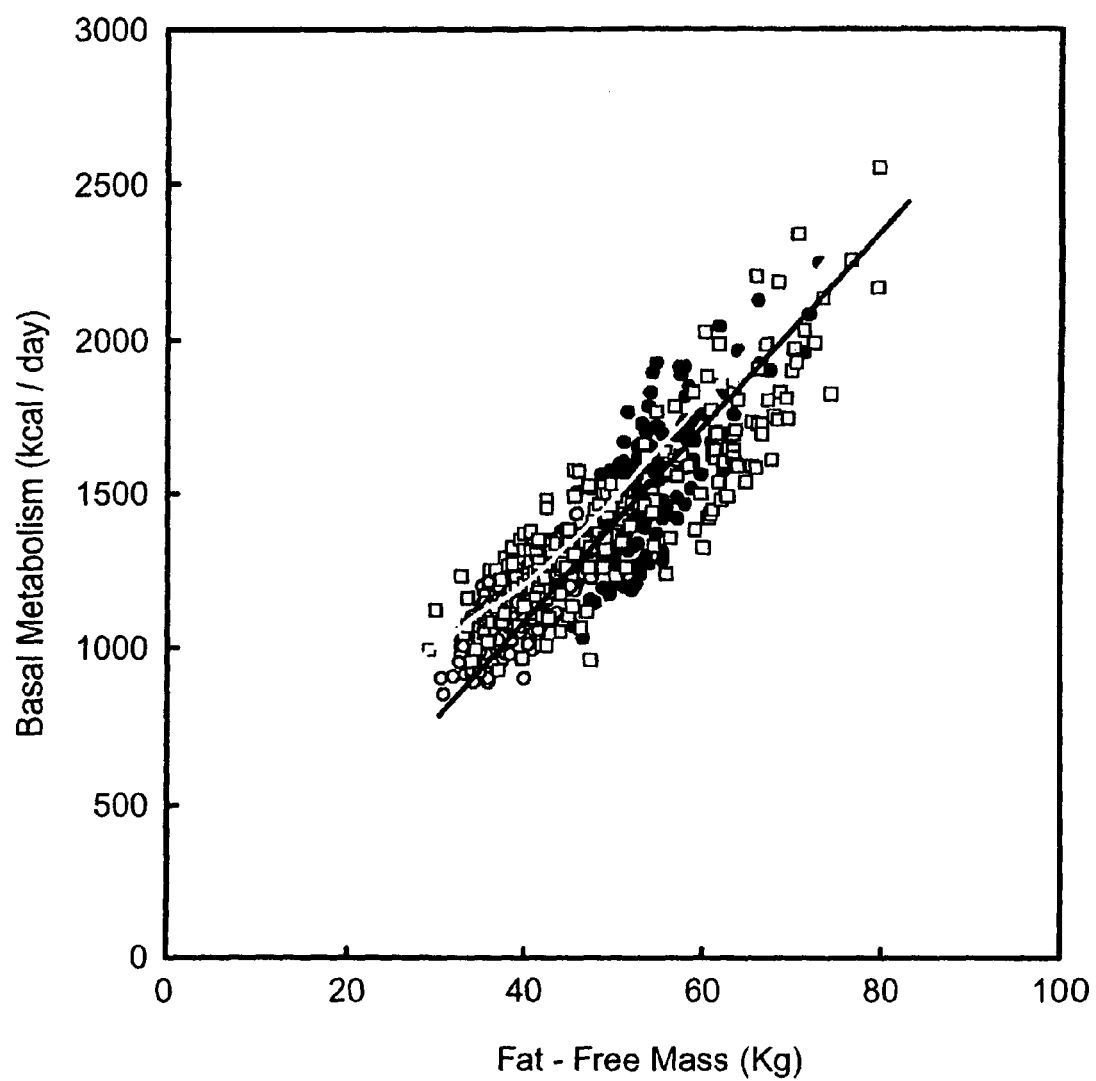
FIG. 5 is a graph illustrating a relationship between basal metabolism and fat-free mass.

As shown in FIG. 5, a calculated value of basal metabolism tends to be lower than an observed value for humans with extremely low fat-free mass. The inventors of the present invention have found that a reciprocal of an age and squared thereof in addition to fat-free mass is preferably utilized when calculating the basal metabolism. In particular, the basal metabolism can be calculated using the following formula:

$$BMR = A_2 \times FFM^2 + B_2 \times FFM + C_2 \times (1/\text{age}) + D_2$$

Where BMR is basal metabolism (kcal/kg), FFM is fat-free mass (kg), and $A_2$, $B_2$, $C_2$ and $D_2$ are constants.

Figure 6:
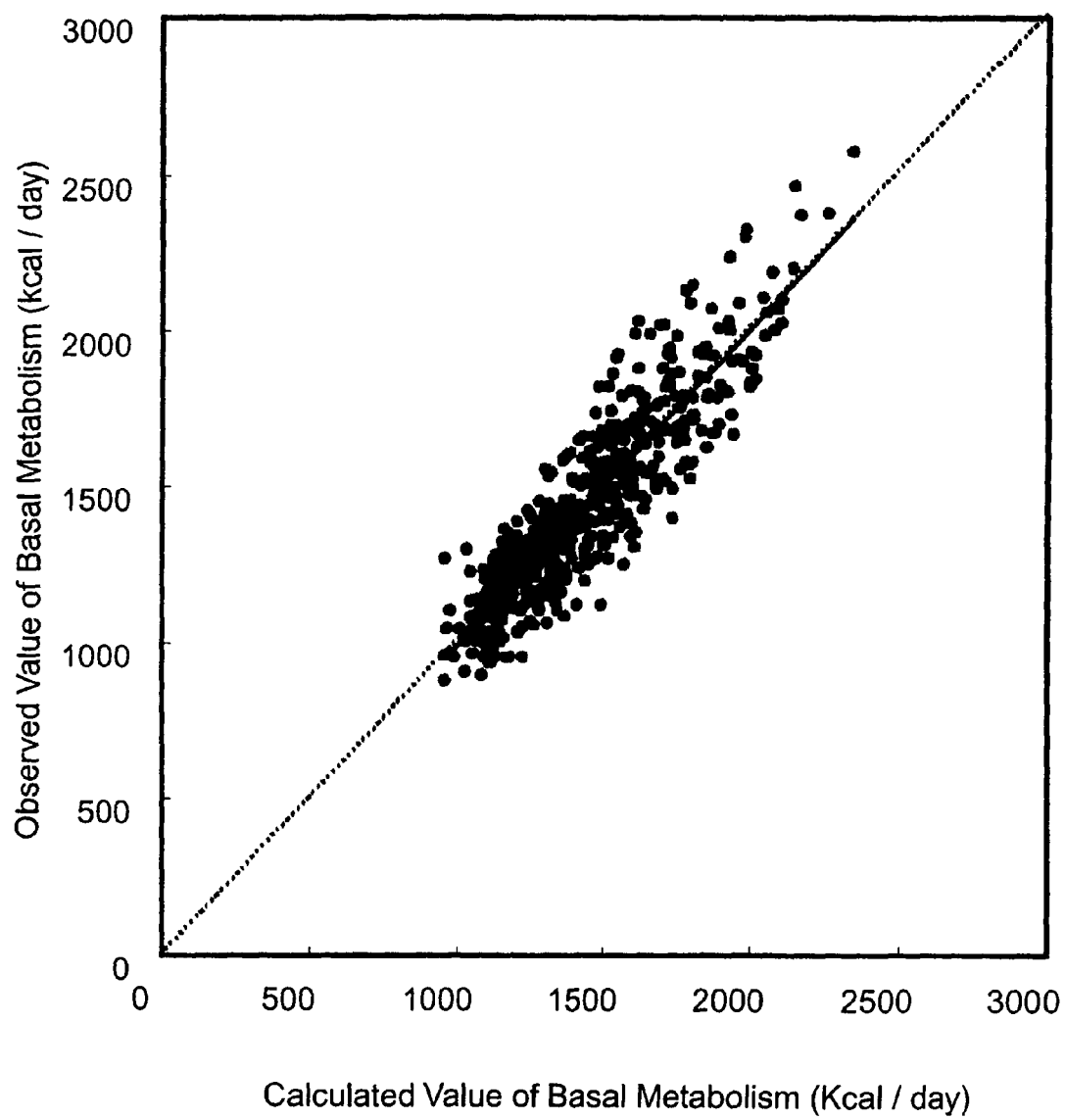
FIG. 6 is a graph illustrating a relationship between observed value of basal metabolism and calculated value of basal metabolism, taking into account of a reciprocal of an age and a squared of fat-free mass.
Figure 7:
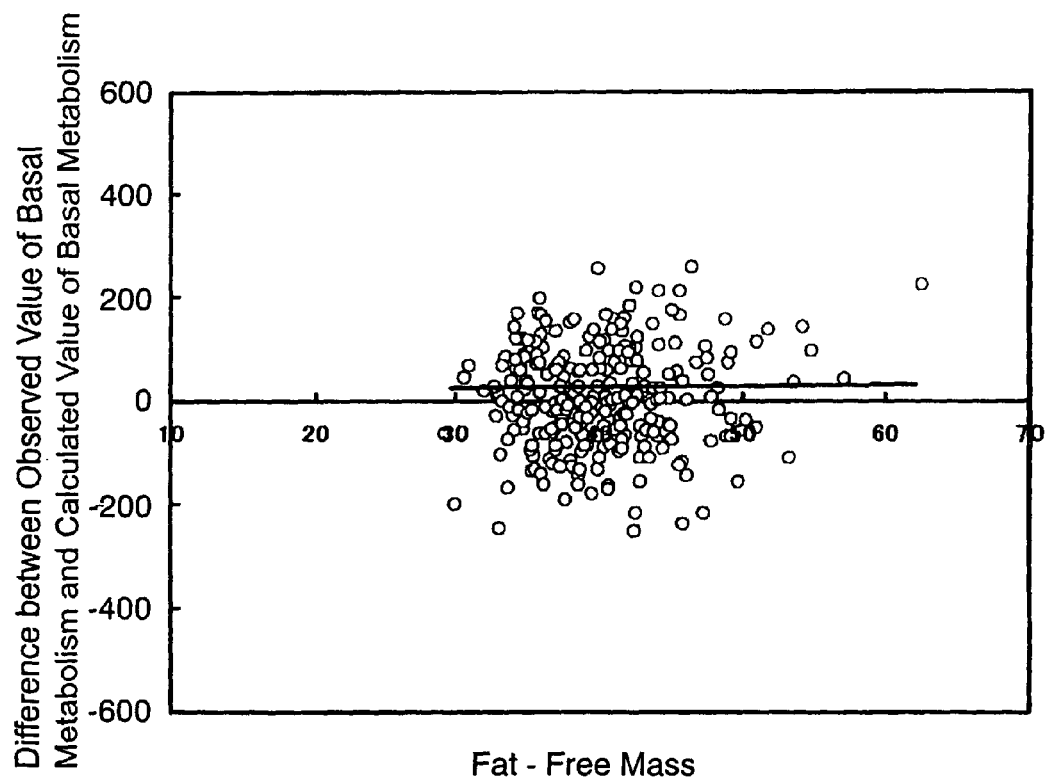
FIG. 7 is a graph illustrating a relationship between difference between observed value of basal metabolism and calculated value of basal metabolism and fat-free mass.

As shown in FIG. 6, a correlation coefficient between the basal metabolism obtained using the above-mentioned formula and the observed basal metabolism is 0.88, which is greatly improved. The observed value was obtained by analysis of expired gas. As shown in FIG. 7, the difference between an observed value and a calculated value against fat-free mass is almost identical.

The inventors of the present invention recognize that the calculated value of basal metabolism tends to be lower than an observed value thereof in humans with low fat-free mass, especially in young slim female and in children. As such the inventors of the present invention have found that a reciprocal of an age and body weight in addition to fat-free mass is preferably utilized to calculate the basal metabolism. In particular, the basal metabolism can be calculated using the following formula:

$$BMR = A_3 \times FFM + B_3 \times (1/\text{age}) + C_3 \times \text{body weight} + D_3$$

Where BMR is basal metabolism (kcal/kg), FFM is fat-free mass (kg), and $A_3$, $B_3$, $C_3$ and $D_3$ are constants.

Figure 8:
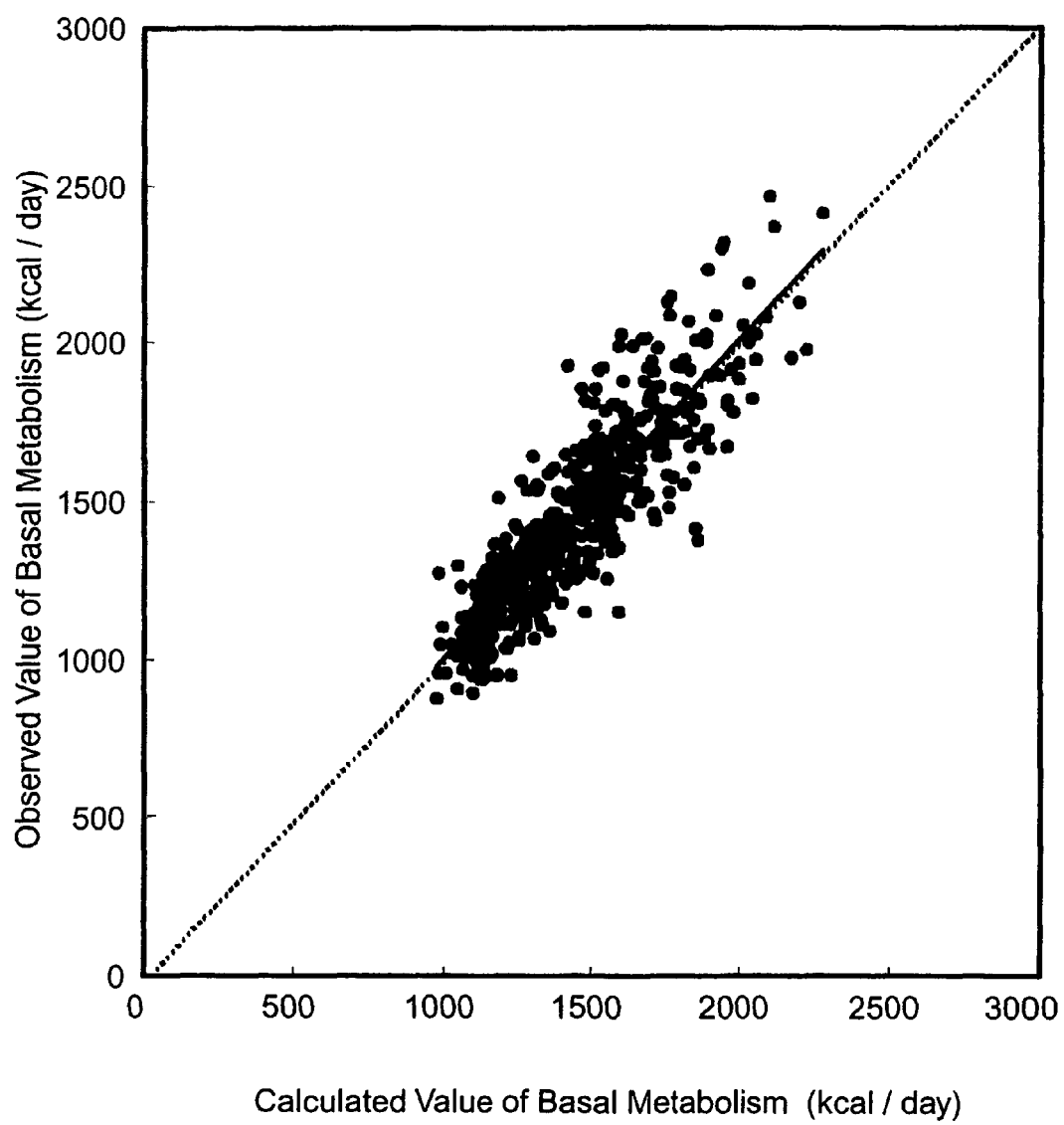
FIG. 8 is a graph illustrating a relationship between observed value of basal metabolism and calculated value of basal metabolism, taking into account of a reciprocal of an age and a body weight.

As shown in FIG. 8, a correlation coefficient between the basal metabolism obtained using the above-mentioned formula and the observed basal metabolism is 0.879. The difference between an observed value and a calculated value against fat-free mass is half of the data shown in FIG. 4.

As shown in FIG. 5, the calculated value of basal metabolism tends to be lower than an observed value thereof in humans with low fat-free mass. The inventors of the present invention have found that a reciprocal of an age, squared thereof and body weight in addition to fat-free mass is preferably utilized to calculate the basal metabolism. In particular, the basal metabolism can be calculated using the following formula:

$$BMR = A_4 \times FFM^2 + B_4 \times FM + C_4 \times (1/\text{age}) + D_4 \times \text{body weight} + E_4$$

Where BMR is basal metabolism (kcal/kg), FFM is fat-free mass (kg), and $A_4$, $B_4$, $C_4$, $D_4$ and $E_4$ are constants.

Figure 9:
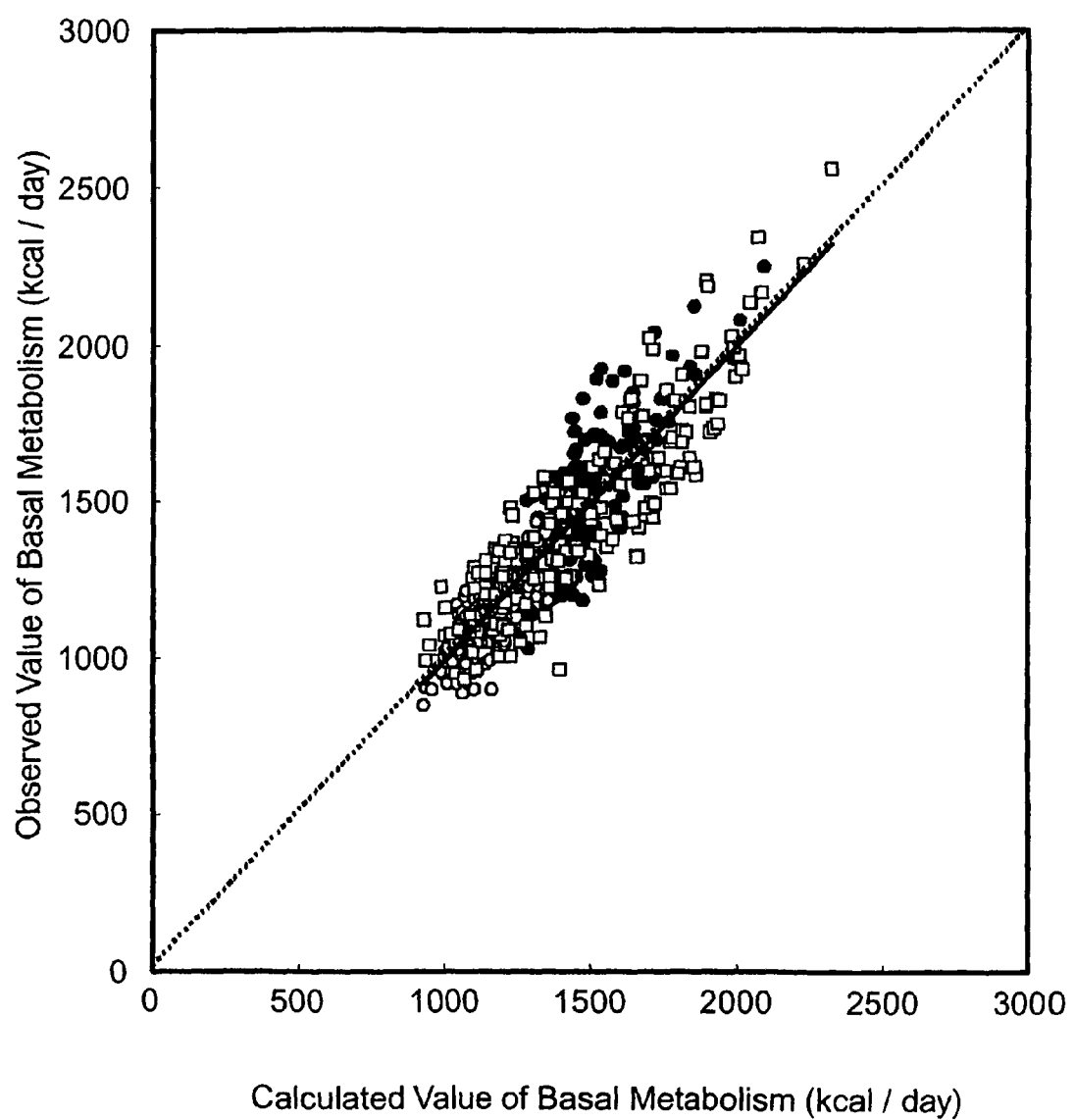
FIG. 9 is a graph illustrating a relationship between observed value of basal metabolism and calculated value of basal metabolism, taking into account of a reciprocal of an age, a squared of fat-free mass and a body weight.

As shown in FIG. 9, a correlation coefficient between the basal metabolism obtained using the above-mentioned formula and the observed basal metabolism is 0.88, which is greatly improved. The observed value was obtained by analysis of expired gas. The difference between an observed value and a calculated value against fat-free mass is substantially identical with the data shown in FIG. 7.

According to the present invention the values for fat-free mass, age and body weight are required to calculate the basal metabolism. The basal metabolism can, therefore, be determined, for example, by changing a control program of a commercially available body fat measuring apparatus with weighing unit or an body fat measurement apparatus in which a value of body weight is manually entered.

Any method of determining fat-free mass is acceptable for use with the invention, for example, a bioimpedance analysis method (BIA method), a DEXA method, a method using a caliper, and the like may be employed.

In addition, a basal metabolism measurement apparatus with an expiration-collecting mask may be used for obtaining the basal metabolism.

For easy understanding, the apparatus of the present invention displays any change in living body characteristic of a person as calculated in the manner as above or it displays any deviation to the standard value of such living body characteristic.

Alternatively the apparatus of the present invention may perform more proper evaluation for any combination of several living body characteristics to provide the optimum advice information to a person to be measured.

Now, one embodiment of the present invention will be described in detail.

A standard value of basal metabolism according to age issued by Former Ministry of Health and Welfare (basal metabolism per body weight: kcal/kg) changes with the years, as shown in FIG. 10. In the embodiment of the present invention, however, the standard values of basal metabolism interpolated so that they are linearly changed with the years are used. As the result of using such interpolated values it becomes possible to use more suitable standard values of basal metabolism for the age that is a personal data of a person to be measured.

For measurement of body fat rate and visceral fat area, several types of measurement apparatus are commercially available, and therefore, they are used to measure body fat rate and visceral fat area in the embodiment of the present invention.

Figure 11:
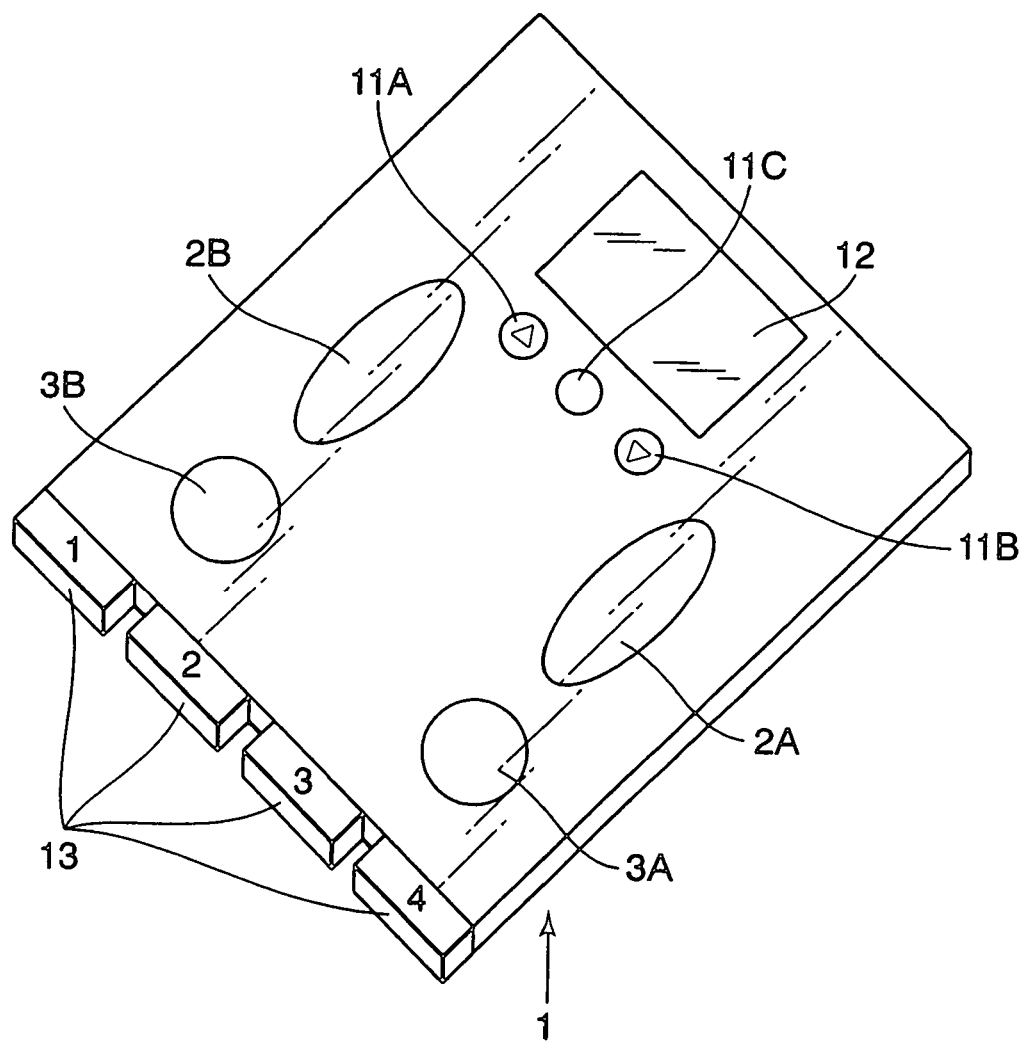
FIG. 11 is an external view illustrating an apparatus for measurement of a living body according to one embodiment of the present invention.
Figure 12:
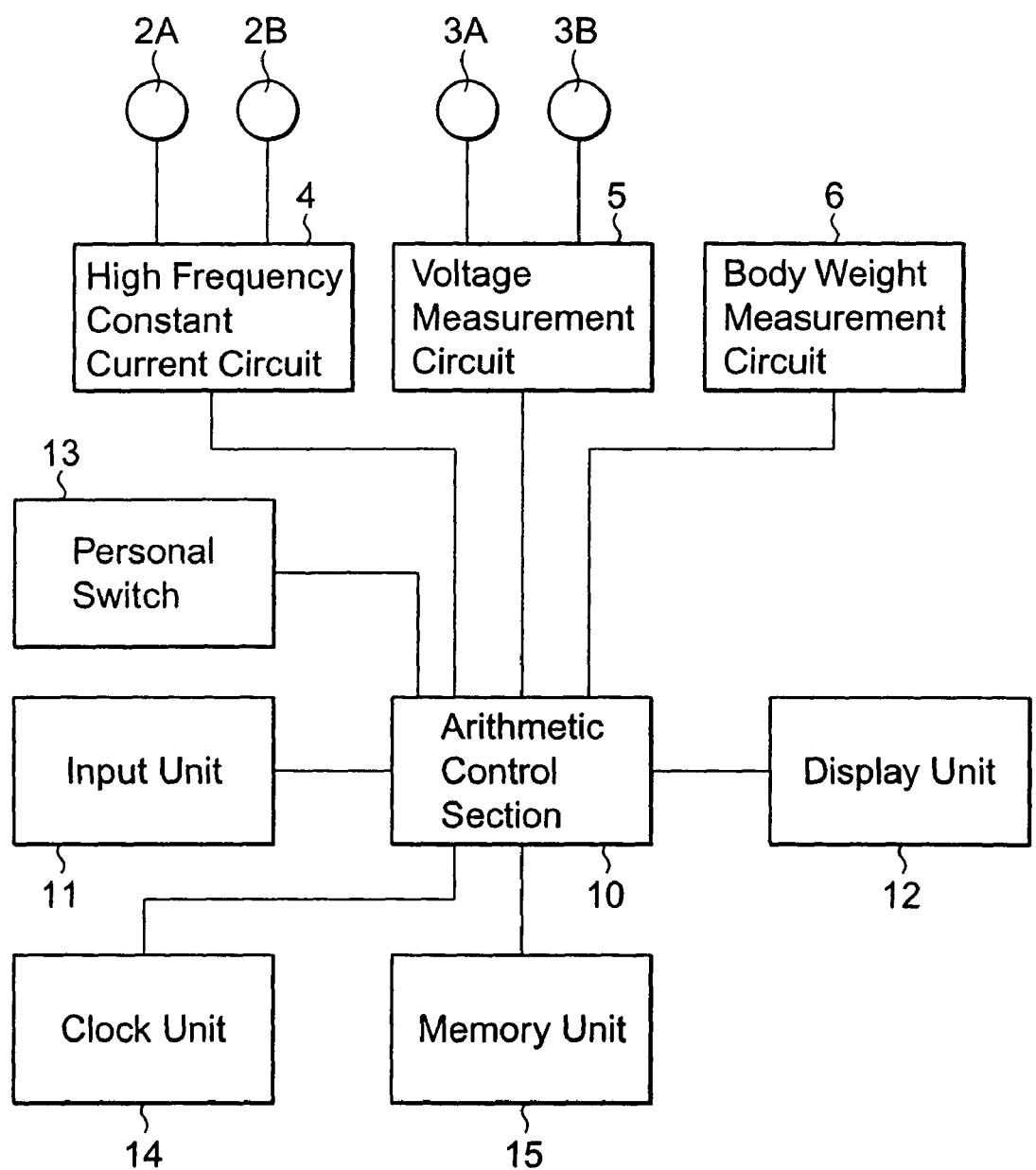
FIG. 12 is a block diagram illustrating internal connection of the components of the apparatus FIG. 11.

FIG. 11 is an external view illustrating an apparatus 1 for measurement of a living body according to one embodiment of the present invention. FIG. 12 is a block diagram illustrating internal connection of the components of the apparatus 1 for measurement of a living body in FIG. 11.

The apparatus 1 for measurement of a living body includes four electrodes on an upper surface thereof. In particular, they consists of a pair of current supplying electrodes 2A, 2B and a pair of voltage measurement electrodes 3A, 3B arranged as an impedance measurement means for measuring the impedance between both feet of a person to be measured The pair of current supplying electrodes 2A, 2B are connected to a high frequency constant current circuit 4 for supplying a weak high frequency constant current. Another pair of voltage measurement electrodes 3A, 3B are connected to a voltage measurement circuit 5 for measuring any voltage drop produced by the constant current. The apparatus 1 further includes a body weight measurement circuit 6 for measuring body weight of a person to be measured when he mounts on the apparatus 1. The voltage measurement circuit 5 and the body weight measurement circuit 6 are connected to an arithmetic control circuit 10 having capability of converting analog to digital values, of calculating body fat mass and basal metabolism and of performing several controls.

A personal data input unit 11 includes three switches: an up switch 11A, a down switch 11B and a setting switch 11C.

The apparatus further includes a display unit 12 for displaying the entered personal data, the measured body weight, and the calculated body fat rate and basal metabolism. In addition, personal measurement switches 13 are mounted on a front-end portion of the apparatus 1.

The apparatus 1 further includes a dock unit 14 for measuring the current date and time, and a memory unit 15 for storing the personal data for several persons, the measured body weight and bioelectrical impedance.

Next, an operation of the apparatus for measurement of a living body will be described, but rather briefly, because measurement and calculation of body fat rate can be found in the Japanese Patent Publication No. 5-49050, for example, and the corresponding products are commercially available.

Figure 13:
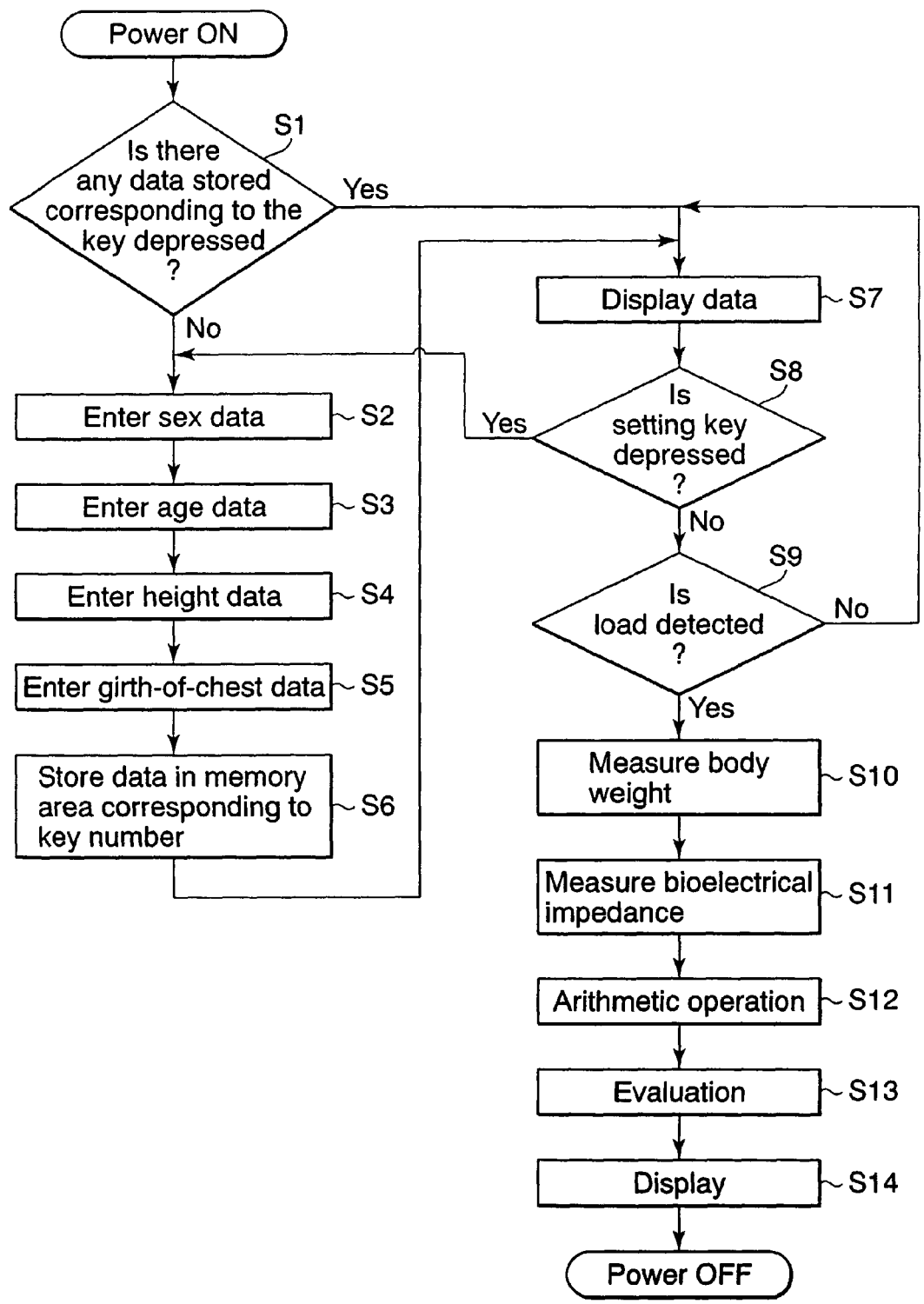
FIG. 13 is a flow chart illustrating a main operation sequence of the apparatus for measurement of a living body.

FIG. 13 is a flow chart illustrating an operation sequence of the apparatus 1 for measurement of a living body.

When a user measures with the apparatus 1 for the first time then it is necessary to conduct setting of personal data in advance.

When any one of the personal measurement switches 13 is depressed then the apparatus 1 for measurement of a living body is turned ON. Then a check is made to determine whether there is the personal data set in the memory area corresponding to the personal measurement switch depressed (Step S1).

If there is no data set the routine enters setting mode. The user modifies numerical value and information displayed on the display unit 12 with the up switch 11A and the down switch 11B until the correct ones are displayed. Upon which the user depresses the setting switch 11C to enter the personal data into the apparatus. In such way the personal data such as sex, age, height and girth of abdomen is entered (Steps S2 to S5). The personal data thus entered is stored in the memory unit 15 in association with the measurement switch number (Step S6).

After setting the personal data or if it has already been set then some message for prompting the user to mount on the apparatus 1 is displayed (Step S7).

If the setting switch 11 is depressed, here, then the routine proceeds to the setting mode (Step S8). The display in step S7 continues until the body weight measurement circuit 6 detects any load (Step S9).

The user mounts on the apparatus 1 so that the tiptoe and heel of the right foot are contact with the current supplying electrode 2A and the voltage measurement electrode 3A and the tiptoe and heel of the left foot are contact with the current supplying electrode 2B and the voltage measurement electrode 3B. Then the body weight measurement circuit 6 measures the body weight of the user (Step S10).

Then the measurement of bioelectrical impedance is conducted. An AC current from the high frequency constant current circuit 5 flows into the body of the user via the current supplying electrodes 2A, 2B, and the voltage across the voltage measurement electrodes 3A, 3B is measured with the voltage measurement circuit 5. Thereafter, the arithmetic control section 10 calculates the bioelectrical impedance of the user (Step S11).

An arithmetic operation is then conducted, based on the measured body weight and the bioelectrical impedance as well as the personal data stored in the memory unit 15 (Step S12).

From the result of arithmetic operation an evaluation of living body condition of the user is conducted (Step S13) and the display of the evaluation result is produced on the display unit 12 (Step S14). The display has plural patterns that are sequentially displayed each for a period of fixed time.

Then, the display of all items is produced, and after the predetermined time period, it is extinguished and the apparatus 1 is turned OFF.

Next, the arithmetic operation will be described in detail.

Figure 14:
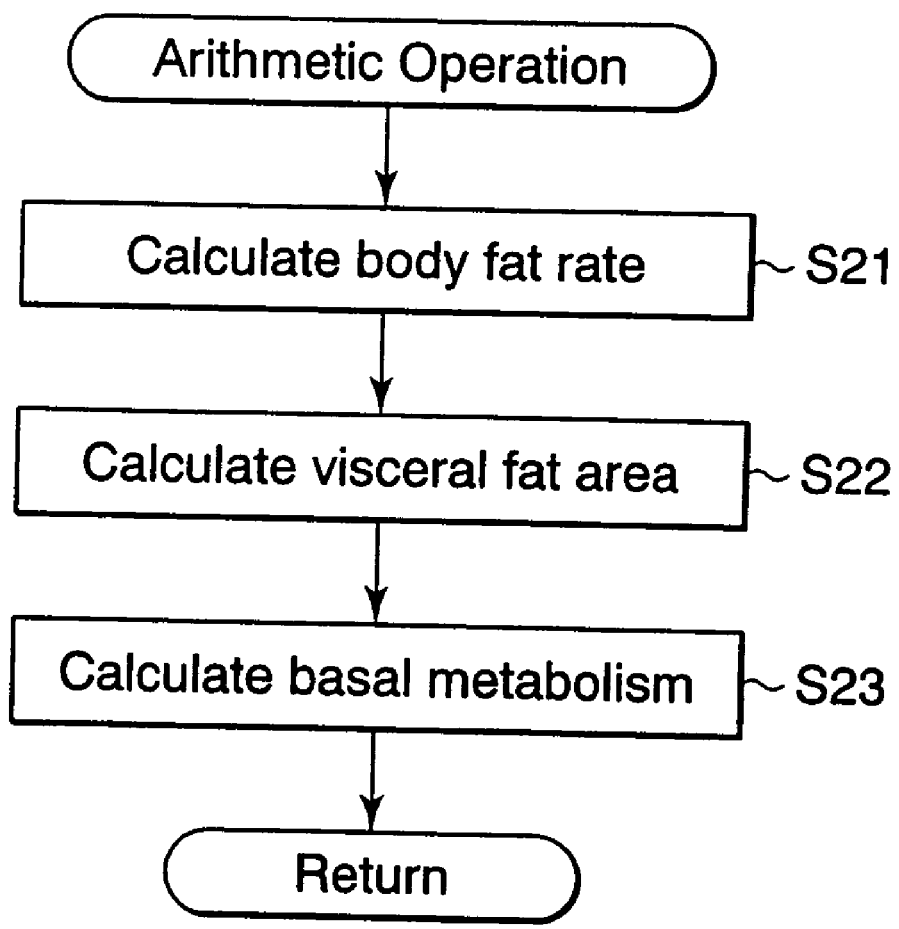
FIG. 14 is a flow chart illustrating an arithmetic operation routine.

FIG. 14 is a flow chart illustrating an arithmetic operation routine. In this routine the body fat rate % Fat is initially calculated (Step S21). As described earlier, the calculation of the body fat rate has been described in the Japanese Patent Publication No. 5-49050, and therefore, no further description is made, here.

Then, the visceral fat area is calculated (Step S22).

The visceral fat area VFA is calculated using the following formula, based on the waist size W(cm), height Ht(cm), body weight Wt(kg) and age:

$$VFA = A_5 W + B_5 Ht/FFC + C_5 (Fat/Ht^2)^2 + D_5 BMI + E_5 Age$$

(where $A_5$, $B_5$, $C_5$, $D_5$ and $E_5$ are constant.)

In the formula FFC is fat-free mass and Fat is body fat mass. The values of fat-free mass and body fat mass are derived when the body fat rate is calculated (Step S21). In addition, BMI is the body mass index that is calculated from "(body weight)/(height)$^2$".

In this way the visceral fat area VFA is calculated.

Next, the basal metabolism is calculated (Step S23).

The calculation of the basal metabolism BMR is performed using any one of four formulas, as described earlier.

Then, the evaluation process will be described in more detail.

Figure 15:
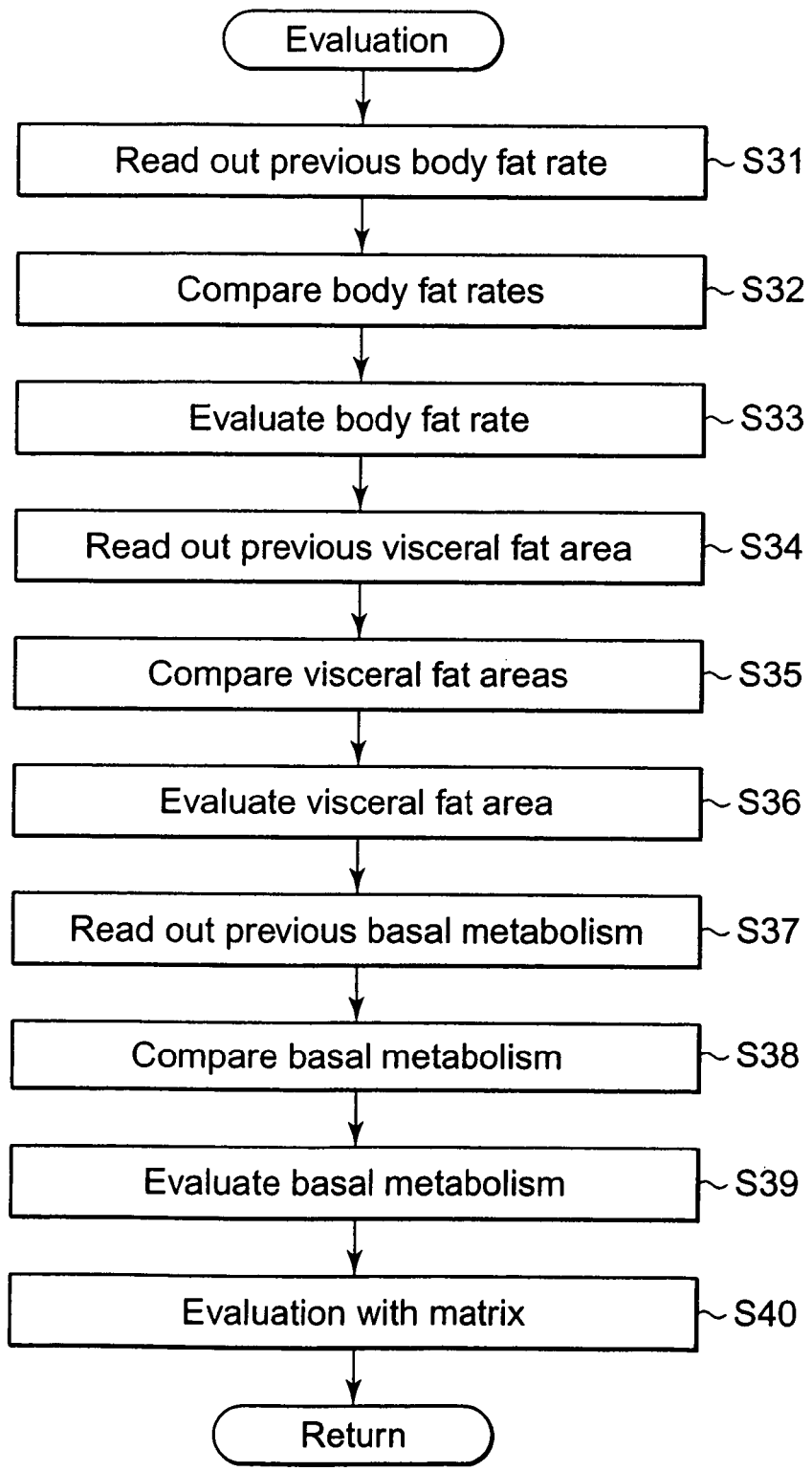
FIG. 15 is a flow chart illustrating an evaluation process routine.

FIG. 15 is a flow chart illustrating an evaluation process routine. At first the previous value of body fat rate is read out from the memory unit 15 (Step S31). The previous value of body fat rate is compared with a calculated value of body fat rate, and depending on the result of comparison, a check is made to determine whether the body fat rate has been increased, decreased or remaining intact without any change (Step S32). Furthermore, the current condition of the body fat rate is evaluated (Step S33). In particular, a check is made to determine whether the body fat rate is higher, lower or standard level, by finding out which of the items in the list of FIG. 16 the body fat rate calculated in Step S21 belongs to, based on the ages and the sex.

Next, the evaluation of visceral fat area is performed. More particularly, the previous value of visceral fat area is read out from the memory unit 15 (Step S34). The previous value of visceral fat area is compared with a calculated value of visceral fat area, and depending on the result of comparison, a check is made to determine whether the visceral fat area has been increased, decreased or remaining intact without any change (Step S35). Furthermore, the current condition of the visceral fat area is evaluated (Step S36). In particular, a check is made to determine whether the visceral fat area is higher, lower or standard level, by finding out which of the items in the list of FIG. 17 the visceral fat area calculated in Step S22 belongs to, based on the ages and the sex. The term "visceral fat level" in FIG. 17 is defined as an index derived from the calculated value of visceral fat area in such manner that the level 1 is set at 10 cm$^2$ and is increased by one level with each increase in area of 10 cm$^2$.

Thereafter, the calculation of visceral fat age is performed. The visceral fat age is calculated in the following formula using the visceral fat area VFA:

$$\text{Visceral Fat Age} = A_6 VFA + B_6$$

(where $A_6$ and $B_6$ are constant.)

Next, the previous value of basal metabolism is read out from the memory unit 15 (Step S37). The previous value of basal metabolism is compared with a calculated value of basal metabolism, and depending on the result of comparison, a check is made to determine whether the basal metabolism has been increased, decreased or remaining intact without any change (Step S38). Furthermore, the current condition of the basal metabolism is evaluated (Step S39). In particular, a check is made to determine whether the basal metabolism is higher, lower or standard level, by finding out how much difference is present between the basal metabolism calculated in Step S23 and the corresponding value in the list of FIG. 10, based on the ages and the sex. More precisely, if the difference is within ±10% then the basal metabolism is considered as the standard. If the difference is over +10% then the basal metabolism is considered as higher level, while if the difference is under −10% then the basal metabolism is considered as lower level.

For example, if a user has personal data: 30 years old, male, body weight of 50 kg, and calculated basal metabolism of 1250 kcal, then the basal metabolism per body weight equals to 1250÷50=25.0% cal/kg). When this is compared to the standard value for the male of 30 years old as shown in FIG. 10:

$$(25.0 - 22.3)/22.3 \times 100 = 12.1\%$$

This value of +12.1% is interpreted as "higher level of basal metabolism".

Then, the basal metabolic age is determined. This is an index representing the age of the common people whose basal metabolism corresponds to that of the user. The basal metabolic age is determined using the list in FIG. 18, based on the calculated basal metabolism and the sex.

Then, the evaluation with matrix format is performed. This evaluation process is performed with some combination of the calculated visceral fat area and basal metabolism like a matrix for determining more effective advice for the user. FIG. 19 is a list illustrating one example of advice information with several combinations of visceral fat and basal metabolism. The term "Exercise program recommended" in FIG. 19 indicates an aerobic exercise program suitable for the user according to his basal metabolism and visceral fat. FIG. 20 is a list illustrating a plurality of such exercise programs. Some columns in FIG. 20 indicate different exercise programs concurrently for "day time" and "before going to bed". However, they may be separately indicated according to the time in a day.

Moreover, evaluation of both basal metabolism and BMI in combination can determine more effective advice information for the user. FIG. 21 is a list illustrating one example of advice information with several combinations of basal metabolism and BMI. The term "exercise program" in FIG. 21 indicates a muscle increase exercise or an aerobic exercise program suitable for the user according to his basal metabolism and BMI. The exercise program is similarly selected among those in FIG. 20.

Some examples of evaluation with matrix format will be described hereafter.

If the basal metabolism of the user is evaluated as "higher level" and the level of visceral fat area is less than 10 then the advice information at upper left position in the list of FIG. 19 is selected. The exercise program ①C is selected among those in the list of FIG. 20. Accordingly the message displayed is: "Youthful and healthy-looking, sport-man type, lower dangerous level of visceral fat, and higher level of metabolism. Keep current body shape! Exercise program recommended is stretch exercise for relaxing and muscle training (mainly for abdominal muscle) for keeping body shape for period of 5 min."

If the basal metabolism of the user is at higher level and the level of BMI is less than 18.5 then the advice information at upper left position in the list of FIG. 21 is selected. The exercise program ①C is selected among those in the list of FIG. 20. Accordingly the message displayed is: "Athlete type having a tightened slim body and difficult to be fat. In order to maintain muscle the exercise program recommended is stretch exercise for relaxing and muscle training (mainly for abdominal muscle) for keeping body shape for period of 5 min."

The result of the evaluation process and the corresponding advice information are displayed on the display unit 12 in Step S14.

Figure 22A:
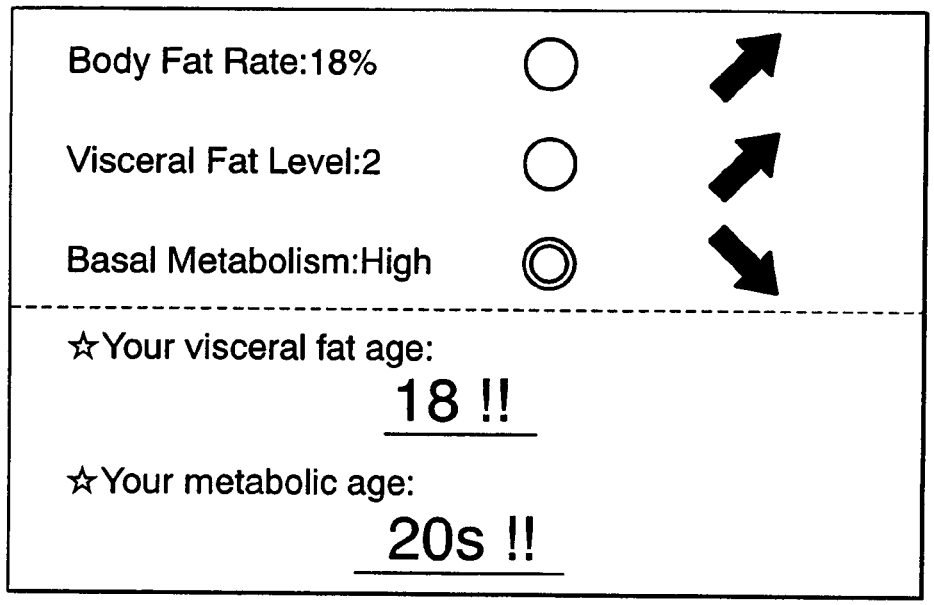
FIGS. 22A and 22B show one example of display illustrating the result of evaluation.
Figure 22B:
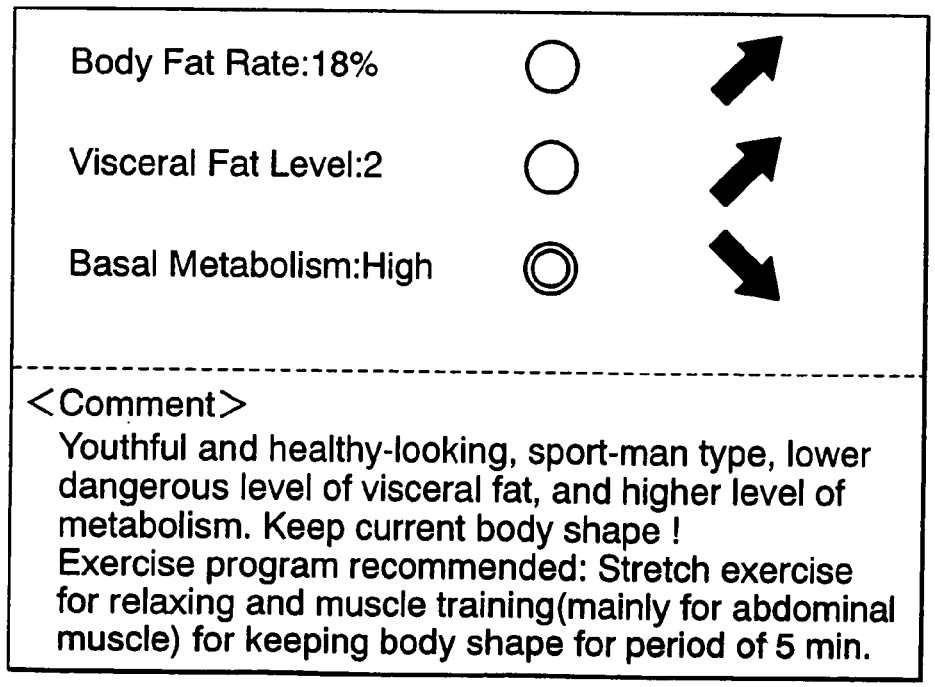

FIGS. 22A and 22B each is a view illustrating one example of the results. In particular, FIG. 22A shows the body fat rate, visceral fat level and basal metabolism displayed in turn from the top.

For the body fat rate the numerical value calculated in Step 21 and the result of evaluation are indicated. When the body fat rate is within the normal range a mark "○" is displayed. Otherwise, a mark "X" is displayed. If it has found by comparison with the previous value in Step S32 that the body fat rate is reduced then "a downward arrow" is displayed. Inversely, if the body fat rate is increased then "an upward arrow" is displayed. Furthermore, if there is no change in body fat rate then "a horizontal arrow" is displayed.

For the visceral fat level the value obtained in evaluation step S36 and the corresponding mark "○", "Δ" or "X" are displayed. In particular, as shown in FIG. 17, the mark "○" means that the visceral fat area is OK; the mark "Δ" means that some slight care is needed; and the mark "X" means that an essential care is needed. For comparison with the previous value the same arrow as that of the body fat rate is used depending on the result obtained in Step S35.

For the basal metabolism "higher", "standard" or "lower" is displayed depending on the result of evaluation in Step S39. If the basal metabolism is higher the mark "⊙" is displayed. If it is standard "○" is displayed. Furthermore, "X" is displayed if it is lower. For comparison with the previous value the same arrow as that of the body fat rate is used.

In addition, the visceral fat age and basal metabolic age determined in the evaluation routine are displayed.

After the predetermined time period elapsed the display is changed to that shown in FIG. 22B. The display in upper portion in which the body fat rate, visceral fat level and basal metabolism are indicated remains identical, but some advice information is additionally displayed in lower portion. The advice information is one that has been determined in evaluation step S40 with the combination of visceral fat and basal metabolism and has been selected among those in the list of FIG. 19. And the exercise program recommended is also one that has been selected among those in the list of FIG. 20.

Although not shown in the figure, after further predetermined time period elapsed, according to the evaluation in matrix format with the combination of basal metabolism and BMI performed in Step S40 of FIG. 15, the advice information selected among those in FIG. 21 and the corresponding exercise program selected among those in FIG. 20 are displayed on the display unit 12 in FIG. 11.

In the embodiment as above the data from the measurement of bioelectrical impedance has been used to calculate the body fat rate, visceral fat area and basal metabolism. However, another embodiment in which the thickness of fat is measured with a caliper may be possible without departing from the scope of the present invention. Now, such embodiment will be described in more detail.

Before describing the principle of the present invention the calculation of the body fat rate is described. The personal data of height, body weight, age and sex is entered, and then, the thickness of subcutaneous fat is entered. Preferably the thickness of subcutaneous fat is measured in the measurement process recommended by Food and Agriculture Organization of the United Nations (abbreviated as FAO) and World Health Organization (abbreviated as WHO) in which a caliper is used for measurement with nipping the skin and the fat tissue thereby at each of two portions of a body, i.e., an upper arm rear portion and an shoulder blade bone lower portion. The inventors of the present invention have defined sum of the measured values as the thickness of subcutaneous fat and calculated the body fat rate of a whole body using either one of the following formulas:

Body Fat Rate =
$$A_7(\text{height}) + B_7(\text{body weight}) + C_7(\text{thickness}) + D_7(\text{age}) + E_7(\text{sex})$$

Where $A_7$, $B_7$, $C_7$, $D_7$ and $E_7$ are constant. Or alternatively, $$\text{Body Fat Rate} = A_8(\text{BMI}) + B_8(\text{thickness}) + C_8(\text{age}) + D_8(\text{sex})$$

Where BMI=(body weight (kg)/height (m))$^2$, and $A_8$, $B_8$, $C_8$ and $D_8$ are constant.

Multiplying the body fat rate by body weight produces body fat mass of a whole body.

Figure 23:
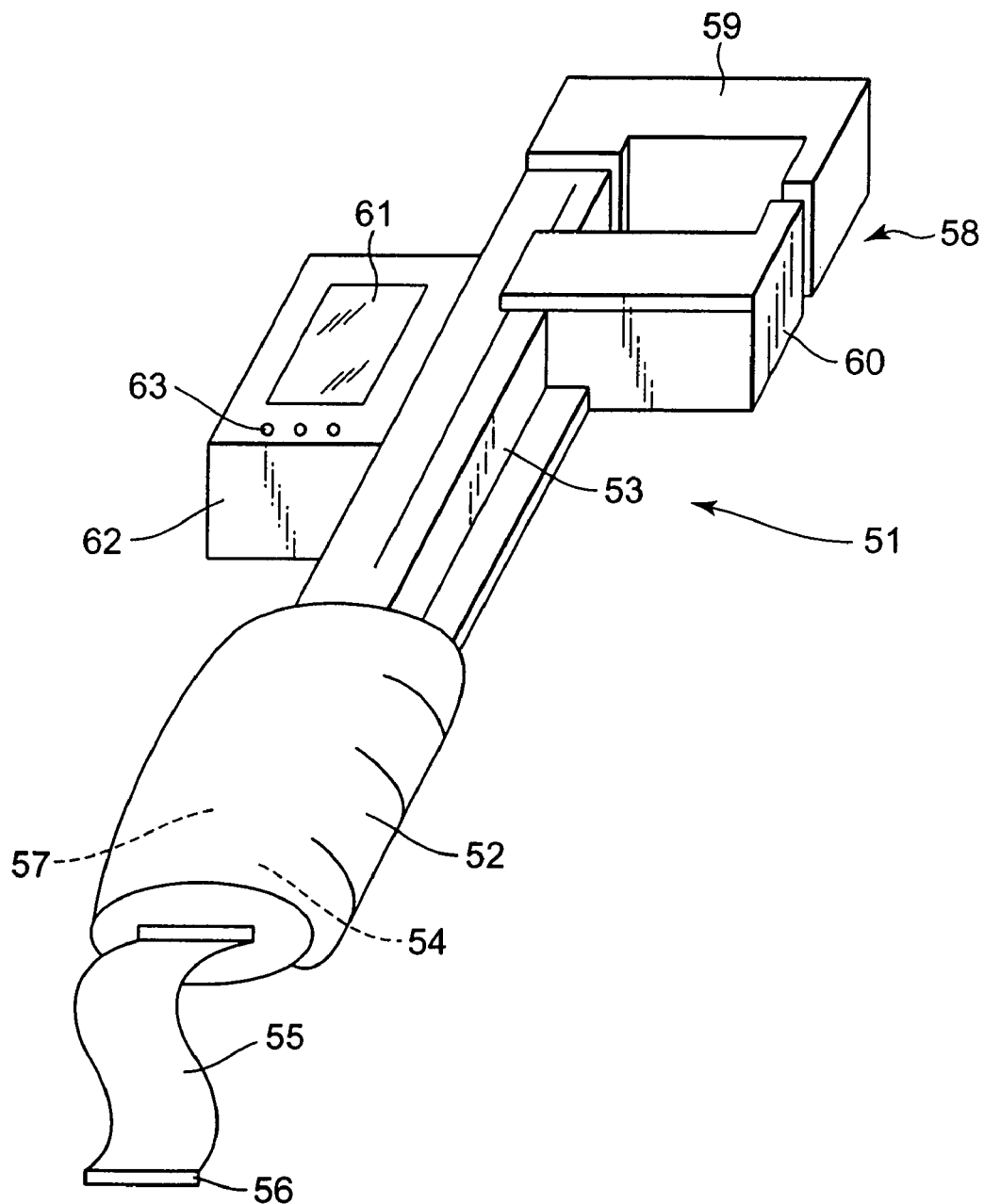
FIG. 23 is an external view of a measurement apparatus for measuring body fat rate and girth of abdomen according to another embodiment of the present invention.

Then, according to the formulas as above, construction and operation of a measurement apparatus will be described with reference to the drawings. FIG. 23 is an external view of a measurement apparatus 51 for measuring the body fat rate and the girth of abdomen according to the present invention. The measurement apparatus 51 includes a grip portion 52 that a user holds with his hand. The grip portion 52 is provided with a support pole 53 at one side thereof for holding a measurement section as described latter and with a digital measure 54 at the other side thereof for measuring the length. The digital measure 54 has a belt 55 and a latch means 56 at the end of the belt 55. The digital measure 54 is designed in such manner that the belt 55 is extended and wound around a user's waist portion or abdominal region passing over a navel, and then the latch means 56 is latched to a counter part 57 (not shown) on the grip portion 52 for measuring the girth of abdomen.

A caliper section 58 is mounted on the end portion of the support pole 53. The caliper section 58 includes a fixed portion 59 securely mounted on an end of the support pole 53 and a movable portion 60 sidably mounted on the support pole 53.

The caliper section 58 measures the thickness of subcutaneous fat with nipping the skin and fat tissue between the fixed portion 59 and the movable portion 60. Although not shown in the figure, each of opposed surfaces of the fixed portion 59 and the movable portion 60 is provided with some detection means including a micro-switch and the like for switching when nipping pressure reaches the predetermined value.

Furthermore, an operation section 62 including a display unit 61 is mounted to the support pole 53 at the side opposite to the movable portion 60. The operation section 62 includes, in addition to the display unit 61, a group of switches 63 mounted on an upper surface for entering various types of data.

Figure 24:
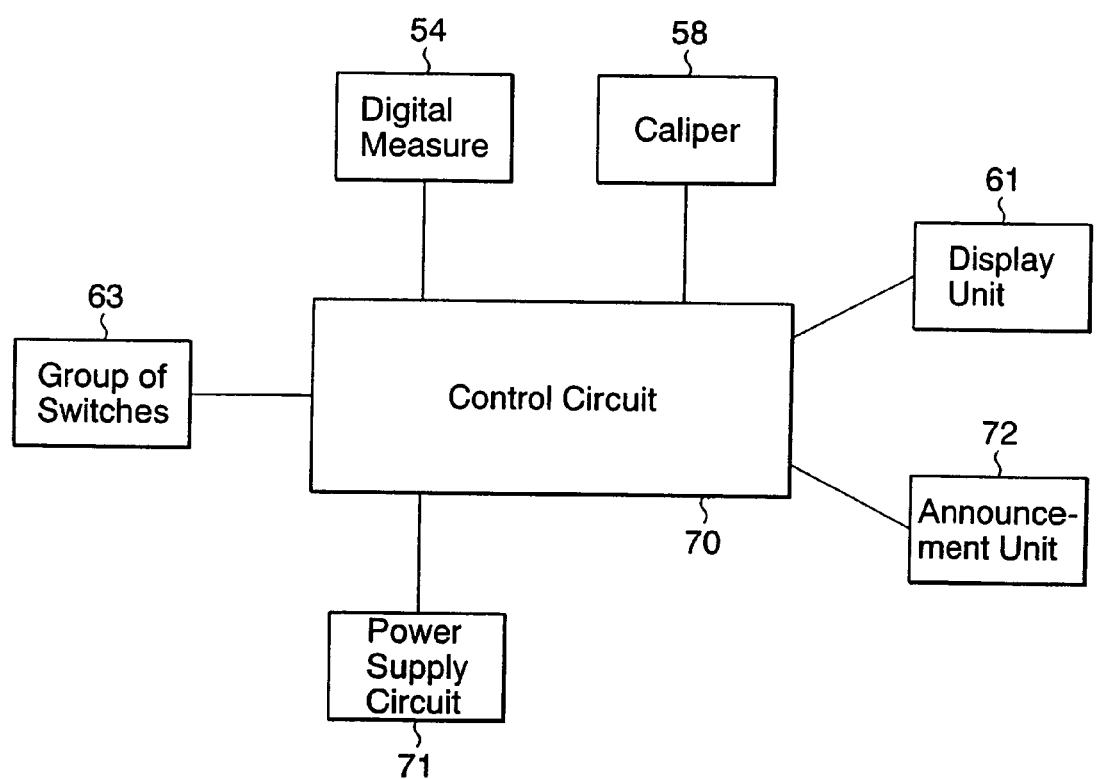
FIG. 24 is a schematic block diagram illustrating main components of the measurement apparatus in FIG. 23.

FIG. 24 is a schematic block diagram illustrating main components of the measurement apparatus 51 as shown in FIG. 23. The central component is a control circuit 70 having a microcomputer, a memory and the like included therein. Connected to this control circuit 70 are: a power supply circuit 71; a display unit 61; a group of switches 63; a digital measure 54; a caliper 58; a detection means 54 including a micro-switch, etc.; and an announcement unit 72 including a buzzer, etc.

Figure 25:
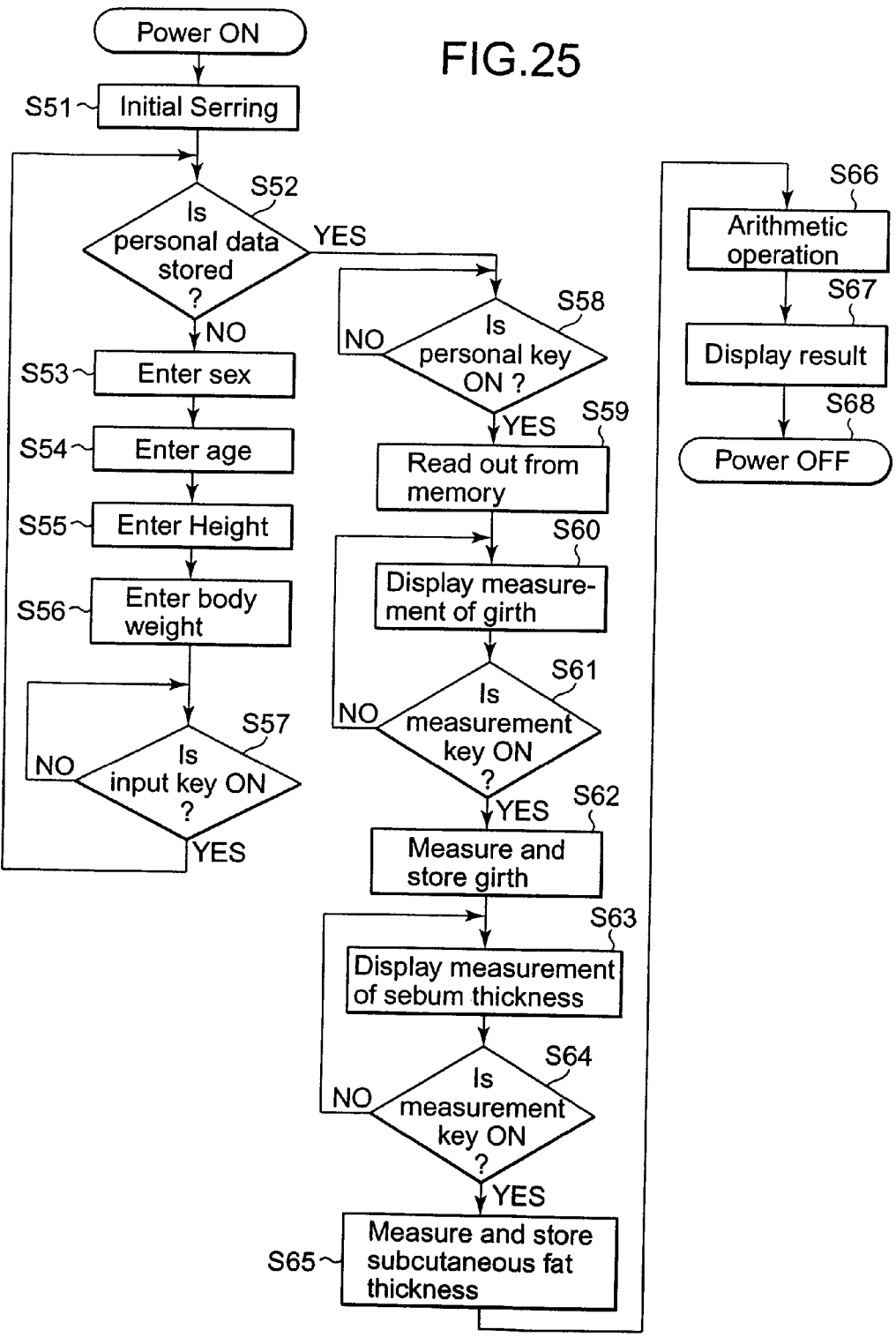
FIG. 25 is a flow chart illustrating a main operation sequence of the apparatus in FIG. 23.

Next, an operation of the measurement apparatus 51 will be described in detail with reference to a flow chart in FIG. 25. Upon switching the power switch (not shown) ON an initial setting of the microcomputer in the control circuit 70 is performed (Step S51). Then, a check is made to determine whether the personal data, for example, sex, age, height, body weight or body build such as athlete type has been stored in the memory or not (Step S52). If not, the routine proceeds to Step S53.

The group of switches 63 is operated to select either male or female, and then, an enter key in the switch group is depressed to enter the data (Step S53). Similarly, the group of switches 63 is operated repeatedly to set each of the numerical values of age, height and body weight and to enter them each time by depressing the enter key in the switch group 63(Step S54 to S56) so that they are stored in the memory in the control circuit 70 (Step S57).

If the personal data has been stored in the memory an affirmative answer is produced in Step S52 to wait for depressing of a personal key in the switch group 63 (Step S58). When the personal key is depressed then the personal data is read out of the memory in the control circuit 70 (Step S59) and some message is displayed on the display unit 61 for prompting a user to measure the girth of his abdomen (Step S60).

According to this message the user winds the belt 55 around his abdomen and depress the measurement switch in the switch group 63. Then, an affirmative answer is produced in Step S61 so that the measurement data of the digital measure 54 is stored in the memory (Step S62).

Thereafter, some message is displayed on the display unit 61 for prompting the user to measure the thickness of subcutaneous fat (Step S63).

According to this message the user operates to slide the movable portion 60 toward the grip portion 52 of the apparatus in FIG. 23, nips the skin and fat tissue between the fixed portion 59 and the movable portion 60 with his fingers, and thereafter, depresses the measurement switch in the switch group 63. Then, an affirmative answer is produced in Step S64 so that the measurement data of the caliper 58 is read and stored in the memory (Step S65).

Next, the calculation of body fat rate is performed using the above-mentioned formulas, based on the stored girth of abdomen, thickness of subcutaneous fat and the personal data of the user.

Then, the calculation and evaluation process of basal metabolism and visceral fat area is conducted (Step S66), but further description thereof is omitted, here, because it is substantially same as in the case of the measurement of bioelectrical impedance as has already been mentioned.

In addition, the result of calculation and evaluation is displayed on the display unit 61 (Step S67), which is also substantially same as in the case of the measurement of bioelectrical impedance as has already been mentioned. Thereafter, the power is turned OFF to end the operation of the measurement apparatus.

In the embodiment as above, the caliper has been used to measure the thickness of subcutaneous fat. Alternatively, any type of other measurement device such as that using ultrasonic wave may be used, as long as it can measure the thickness of subcutaneous fat.

In the embodiment as above, an apparatus having configuration where, in addition to measurement of body weight, bioelectrical impedance is measured between both feet of a user has been described, by way of an example. The present invention, however, is not limited to such configuration. For example, the apparatus may be designed to have another configuration where no measurement of body weight is performed, but only comparison of bioelectrical impedance is performed for evaluation of a user. In this connection, the bioelectrical impedance may be measured between both hands or between hands and feet. Alternatively, a plurality of electrodes may be used to measure the bioelectrical impedance in a plurality of parts of the user's body. In this case, because of increased number of parameters used for comparison, the body composition in each of the parts can be measured and displayed.

In addition, in the embodiment as above, the measurement apparatus has been described to have capability of calculating the body fat rate that is the rate of body fat occupying in the body of a user as an index about the body. However, the measurement apparatus may have different capability of calculating the body fat mass that is the amount of body fat present in the body. Alternatively, the apparatus may calculate the visceral fat mass that is deposited to the surroundings of an organ within the abdominal cavity Furthermore, in the embodiment as above, the measurement apparatus has been described to have such configuration that a measuring unit is included therein for measuring the bioelectrical impedance or body weight, the living body information such as basal metabolism, visceral fat or BMI is calculated based on the measured value of bioelectrical impedance or body weight, and the effective information is displayed. However, the measurement apparatus may be of any calculator type in which measurement of the bioelectrical impedance or body weight is separately or externally performed, the measured value of such living information is manually entered thereto, and various types of evaluation and display is performed based on such entered information.

Furthermore, the present invention is not limited to the shape of the measurement apparatus as has been illustrated and described in the embodiment as above. Rather, the present invention may be applied to different shape of the apparatus such as card type, notebook type or other portable size unit.

Moreover, in the embodiment as above, the content of display has been described to include body fat rate, visceral fat level, basal metabolism, visceral fat age, basal metabolic age and advice information, as shown in FIGS. 22 (A) and 22 (B). The present invention, however, is not limited to such content of display, but the visceral fat area and basal metabolism may directly be displayed, or any other information may be displayed.

Additionally, in the embodiment as above, the apparatus has been described to have such configuration that each time the measurement is made the measured value is stored as the previous value. It may be possible, however, that the measured values for several previous measurements are stored and the average of them is used as the standard value, which is updated each time new measurement is made.

It is apparent from the foregoing that an apparatus for measurement of a living body according to the present invention is advantageous in that the basal metabolism entered by an input unit is compared with the standard values of basal metabolism according to the ages stored in a storage unit for calculating a basal metabolic age indicating what age the basal metabolism of a person to be measured corresponds to. Therefore, the person to be measured can promptly know what age the basal metabolism of the person corresponds to.

Furthermore, an apparatus for measurement of a living body according to the present invention is advantageous in that the latest basal metabolism entered by an input unit is compared with the already stored basal metabolism. Accordingly, the person to be measured can easily understand any change in basal metabolism from the previous measurement to the latest measurement.

Furthermore, an apparatus for measurement of a living body according to the present invention comprises an arithmetic unit for calculating "BMI" on the basis of the personal data, a comparison unit for comparing the basal metabolism entered by an input unit with the standard values of basal metabolism according to the ages stored in a storage unit, and a display unit for displaying the information about the relation between the result of comparison and said "BMI". Therefore, the person to be measured can understand the basal metabolism suitable for his body build.

In addition, according to the present invention, the visceral fat area entered by an input unit is compared with the standard values of visceral fat area according to the ages stored in a storage unit for calculating a visceral fat age indicating what age the visceral fat area of the person to be measured corresponds to. Therefore, the person to be measured can promptly know what age the visceral fat area of the person corresponds to.

Moreover, according to the present invention, the latest visceral fat area entered by an input unit is compared with the visceral fat area already stored in a data storage unit. Accordingly, the person to be measured can easily understand any change in visceral fat area from the previous measurement to the latest measurement.

In addition, according to the present invention, the visceral fat area entered by an input unit is compared with the basal metabolism calculated by an arithmetic unit. Therefore, the person to be measured can easily and totally understand the result of measurement in view of two factors.

What is claimed is:

1. An apparatus for measurement of a living body, comprising:
    a personal data input unit;
    a non-transitory standard value storage unit;
    an arithmetic control section;
    a display unit; and
    a non-transitory advice information storage unit, wherein:
        said personal data input unit is configured to acquire at least weight, height and age of a person to be measured,
        said arithmetic control section is configured to calculate a basal metabolism of the person to be measured,
        said non-transitory standard value storage unit is configured to store standard values of basal metabolism according to ages,
        said arithmetic control section is configured to calculate a BMI of the person to be measured on the basis of the personal data,
        said arithmetic control section is configured to compare the basal metabolism calculated by said arithmetic control section with the standard values of basal metabolism according to ages stored in said non-transitory standard value storage unit,
        said display unit is configured to display information about a relation between a result of comparison and the calculated BMI,
        said non-transitory advice information storage unit is configured to store advice information according to the relation between basal metabolism and BMI,
        said arithmetic control section is configured to select the advice information for the person to be measured based on the result of comparison and said calculated BMI, and
        said display unit is configured to display the selected advice information.

2. The apparatus for measurement of a living body according to claim 1, wherein:
    said advice information stored in said non-transitory advice information storage unit includes at least one of advice information for type of exercise, content of exercise and time interval of exercise suitable for the age of the person to be measured.

3. The apparatus for measurement of a living body according to any of claims 1 to 2, wherein:
    said arithmetic control section is configured to calculate a basal metabolic age indicating what age the basal metabolism of the person to be measured corresponds to, and
    said display unit is configured to display information about the calculated basal metabolic age.

* * * * *